US012558047B2

(12) United States Patent
Shiraishi et al.

(10) Patent No.: US 12,558,047 B2
(45) Date of Patent: Feb. 24, 2026

(54) MEDICAL IMAGE PROCESSING APPARATUS, X-RAY DIAGNOSIS APPARATUS, AND NON-VOLATILE COMPUTER-READABLE STORAGE MEDIUM STORING THEREIN MEDICAL IMAGE PROCESSING PROGRAM

(71) Applicant: CANON MEDICAL SYSTEMS CORPORATION, Otawara (JP)

(72) Inventors: Kunio Shiraishi, Otawara (JP); Masanori Matsumoto, Nasushiobara (JP); Hisato Takemoto, Nasushiobara (JP); Shingo Ogura, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 462 days.

(21) Appl. No.: 18/056,904

(22) Filed: Nov. 18, 2022

(65) Prior Publication Data

US 2023/0165554 A1 Jun. 1, 2023

(30) Foreign Application Priority Data

Nov. 30, 2021 (JP) ................................. 2021-193919

(51) Int. Cl.
*A61B 6/00* (2024.01)
(52) U.S. Cl.
CPC .............. *A61B 6/48* (2013.01); *A61B 6/4441* (2013.01); *G06T 2207/30101* (2013.01)
(58) Field of Classification Search
CPC ....... A61B 6/48; A61B 6/4441; A61B 6/0407; A61B 6/469; A61B 6/03; A61B 6/504;

(Continued)

(56) References Cited

U.S. PATENT DOCUMENTS

2001/0007593 A1* 7/2001 Oosawa ................. G16H 30/20
382/294
2001/0010732 A1* 8/2001 Oosawa .................... G06T 7/32
382/128

(Continued)

FOREIGN PATENT DOCUMENTS

JP 2015-93131 A 5/2015
JP 2020-146333 A 9/2020

OTHER PUBLICATIONS

Japanese Office Action issued Aug. 5, 2025 in Japanese Patent Application No. 2021-193919, 2 pgs.

*Primary Examiner* — Iriana Cruz
(74) *Attorney, Agent, or Firm* — Oblon, McClelland, Maier & Neustadt, L.L.P.

(57) ABSTRACT

A medical image processing apparatus according to an embodiment includes processing circuitry. The processing circuitry is configured: to perform registration between one contrast image and each of a plurality of mask images; to calculate a plurality of matching degrees between the plurality of mask images and the one contrast image registered with each other, on the basis of the plurality of mask images and the one contrast image registered with each other; and to determine a difference between one of the mask images corresponding to a maximum matching degree among the plurality of matching degrees and the one contrast image, as one subtraction image corresponding to the one contrast image.

14 Claims, 9 Drawing Sheets

(58) Field of Classification Search
CPC ... A61B 6/4208; A61B 6/5241; A61B 6/5235;
A61B 6/481; G06T 2207/30101
See application file for complete search history.

(56)                    References Cited

U.S. PATENT DOCUMENTS

| 2016/0239972 | A1* | 8/2016 | Zhu ......................... G06T 7/337 |
| 2016/0253803 | A1* | 9/2016 | Miyamoto ............. A61B 6/504 |
| | | | 382/132 |
| 2017/0367673 | A1* | 12/2017 | Ohishi ................... G16H 50/30 |
| 2021/0232806 | A1* | 7/2021 | He ....................... G06V 40/171 |

* cited by examiner

FIG.3

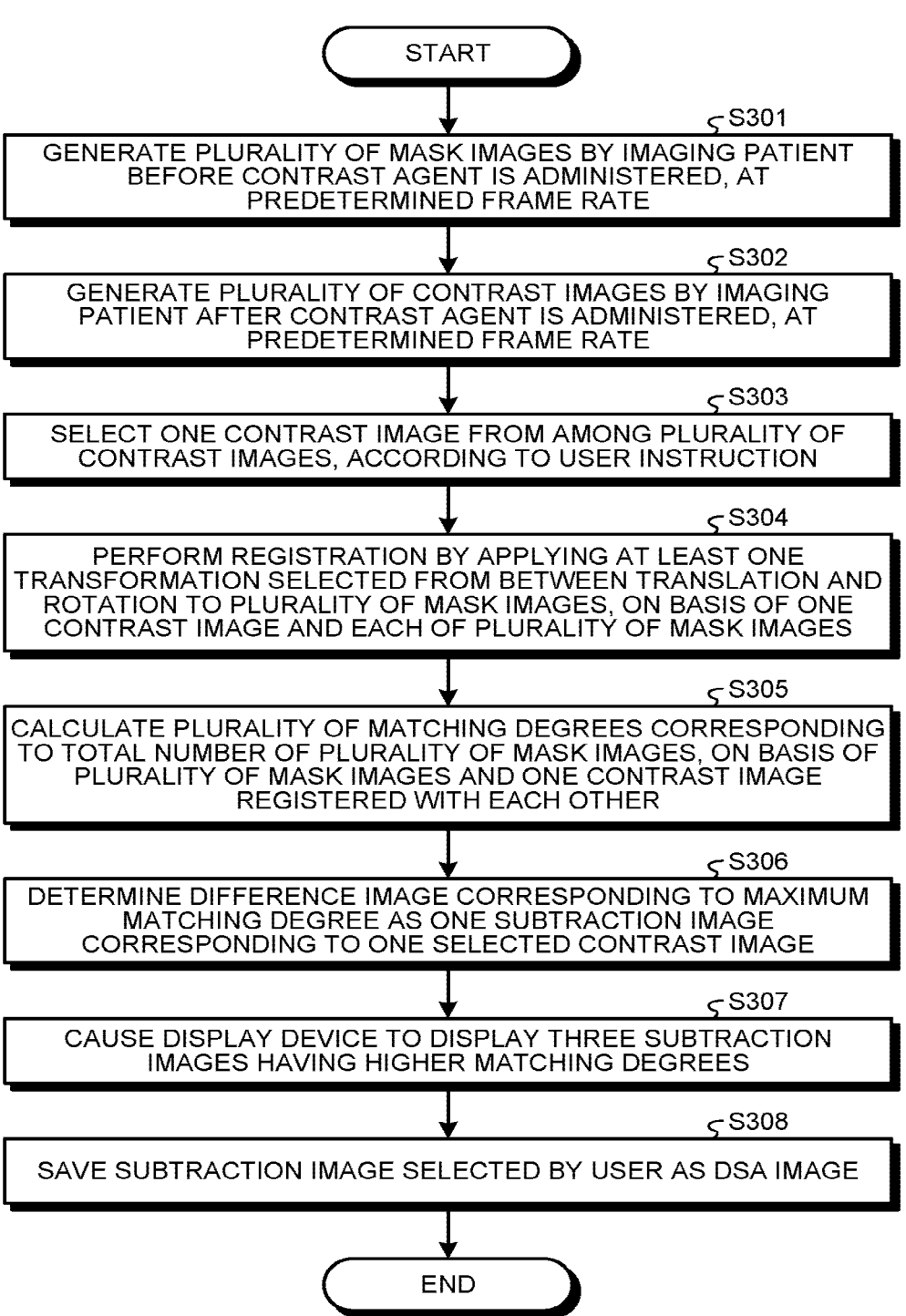

START

S301
GENERATE PLURALITY OF MASK IMAGES BY IMAGING PATIENT BEFORE CONTRAST AGENT IS ADMINISTERED, AT PREDETERMINED FRAME RATE

S302
GENERATE PLURALITY OF CONTRAST IMAGES BY IMAGING PATIENT AFTER CONTRAST AGENT IS ADMINISTERED, AT PREDETERMINED FRAME RATE

S303
SELECT ONE CONTRAST IMAGE FROM AMONG PLURALITY OF CONTRAST IMAGES, ACCORDING TO USER INSTRUCTION

S304
PERFORM REGISTRATION BY APPLYING AT LEAST ONE TRANSFORMATION SELECTED FROM BETWEEN TRANSLATION AND ROTATION TO PLURALITY OF MASK IMAGES, ON BASIS OF ONE CONTRAST IMAGE AND EACH OF PLURALITY OF MASK IMAGES

S305
CALCULATE PLURALITY OF MATCHING DEGREES CORRESPONDING TO TOTAL NUMBER OF PLURALITY OF MASK IMAGES, ON BASIS OF PLURALITY OF MASK IMAGES AND ONE CONTRAST IMAGE REGISTERED WITH EACH OTHER

S306
DETERMINE DIFFERENCE IMAGE CORRESPONDING TO MAXIMUM MATCHING DEGREE AS ONE SUBTRACTION IMAGE CORRESPONDING TO ONE SELECTED CONTRAST IMAGE

S307
CAUSE DISPLAY DEVICE TO DISPLAY THREE SUBTRACTION IMAGES HAVING HIGHER MATCHING DEGREES

S308
SAVE SUBTRACTION IMAGE SELECTED BY USER AS DSA IMAGE

END

MATCHING DEGREES

DISPLAY EXAMPLES

NUMBER OF FRAMES OF
MASK IMAGES

DISPLAY EXAMPLES

NUMBER OF FRAMES OF
CONTRAST IMAGES

DISPLAY EXAMPLES

NUMBER OF FRAMES OF
CONTRAST IMAGES

MEDICAL IMAGE PROCESSING APPARATUS, X-RAY DIAGNOSIS APPARATUS, AND NON-VOLATILE COMPUTER-READABLE STORAGE MEDIUM STORING THEREIN MEDICAL IMAGE PROCESSING PROGRAM

CROSS-REFERENCE TO RELATED APPLICATIONS

This application is based upon and claims the benefit of priority from Japanese Patent Application No. 2021-193919, filed on Nov. 30, 2021, the entire contents of which are incorporated herein by reference.

FIELD

Embodiments described herein relate generally to a medical image processing apparatus, an X-ray diagnosis apparatus, and a non-volatile computer-readable storage medium storing therein a medical image processing program.

BACKGROUND

Conventionally, when Digital Subtraction Angiography (DSA) is performed for a patient who has difficulty in holding his/her breath during abdomen imaging or the like using an X-ray cardiovascular diagnosis apparatus, a plurality of mask images are acquired over a plurality of frames so that a user selects an optimal mask image for a contrast image from among the plurality of mask images and thus generates a DSA image. When the user is to visually select optimal mask images for contrast images, however, a problem arises where working for a long period of time may impose a burden on the user.

To cope with this situation, an X-ray cardiovascular diagnosis apparatus may be configured to evaluate similarity between such a contrast image and a plurality of mask images so as to select one of the mask images having the highest similarity as an optimal mask image for the DSA image. In that situation, image quality of the generated DSA image may be degraded due to an error in a position alignment (hereinafter "registration") between the contrast image and the selected mask image.

BRIEF DESCRIPTION OF THE DRAWINGS

FIG. 3 is a flowchart illustrating an example of a procedure in a DSA image determining process according to the embodiment;

DETAILED DESCRIPTION

Figure 1:
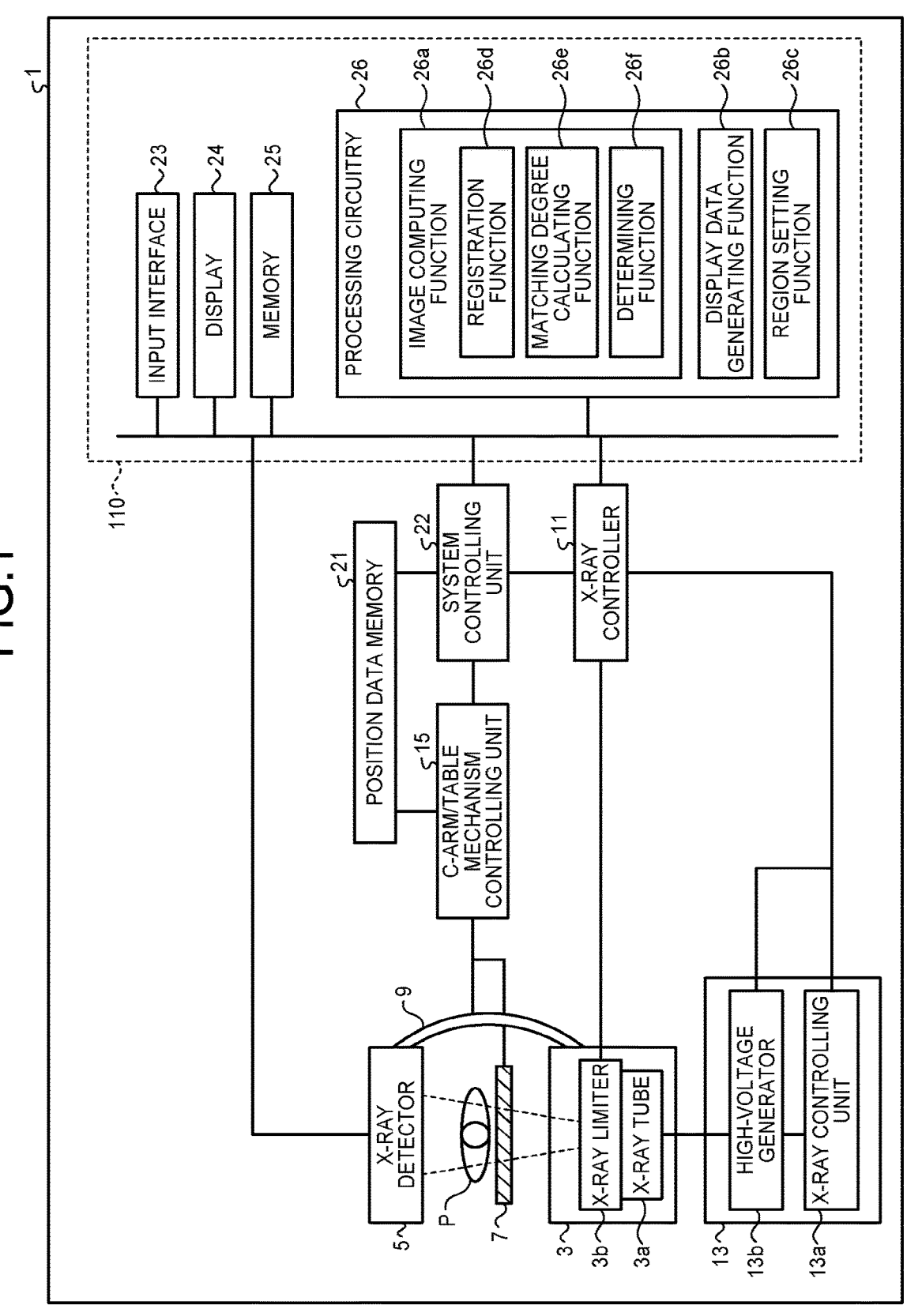
FIG. 1 is a block diagram illustrating a configuration of an X-ray diagnosis apparatus according to an embodiment.

A medical image processing apparatus according to an embodiment includes processing circuitry. The processing circuitry is configured: to perform registration between one contrast image and each of a plurality of mask images; to calculate a plurality of matching degrees between the plurality of mask images and the one contrast image registered with each other, on the basis of the plurality of mask images and the one contrast image registered with each other; and to determine a difference between one of the mask images corresponding to a maximum matching degree among the plurality of matching degrees and the one contrast image, as one subtraction image corresponding to the one contrast image.

Exemplary embodiments of a medical image processing apparatus, an X-ray diagnosis apparatus, and a medical image processing program will be explained below with reference to the accompanying drawings. In the following embodiments, some of the elements referred to by using the same reference characters are assumed to perform the same operations, and duplicate explanations thereof will be omitted as appropriate. Further, the description of each of the embodiments is, in principle, similarly applicable to modification examples and the like.

EMBODIMENTS

FIG. 1 is a block diagram illustrating a configuration of an X-ray diagnosis apparatus 1 according to an embodiment. The X-ray diagnosis apparatus 1 includes, as a data acquisition system, an X-ray generating unit 3, an X-ray detector 5, a table 7, a C-arm 9, an X-ray controller 11, a high-voltage generating unit 13, and a C-arm/table mechanism controlling unit 15. The X-ray diagnosis apparatus 1 includes, as a data processing system, a position data memory 21, a system controlling unit 22, an input interface 23, a display 24, a memory 25, and processing circuitry 26.

The X-ray generating unit 3 includes an X-ray tube 3a and an X-ray limiter 3b. The X-ray tube 3a is a vacuum tube configured to generate X-rays. The X-ray tube 3a is configured to generate the X-rays by accelerating thermo electrons emitted from a negative pole (a filament) with high voltage and causing the accelerated electrons to collide with a tungsten positive pole.

The X-ray limiter 3b is positioned between the X-ray tube 3a and the X-ray detector 5 and is configured by using metal plates such as lead plates. The X-ray limiter 3b is controlled by the X-ray controller 11. The X-ray limiter 3b is configured to block X-rays outside an opening region. As a result, the X-ray limiter 3b is configured to narrow down the X-rays generated by the X-ray tube 3a so as to be emitted onto a region of interest of an examined subject (hereinafter, "patient") P. For example, the X-ray limiter 3b has a plurality of limiting blades. By sliding these limiting blades, the X-ray limiter 3b is configured to adjust the region where the X-rays are blocked so as to have an arbitrary size. The limiting blades of the X-ray limiter 3b are driven by a driving device (not illustrated) under the control of the X-ray controller 11 in accordance with the region of interest set by a region setting function 26c.

The X-ray detector 5 is configured to detect the X-rays generated by the X-ray tube 3a. For example, the X-ray detector 5 is configured to detect X-rays that have passed through the patient P. It is possible to use the X-ray detector 5 of a direct conversion type configured to directly convert the X-rays into an electric charge or of an indirect conversion type configured to convert the X-rays into light and to further convert the light into an electric charge. In the following sections, as an example, the X-ray detector 5 will be described as being of the direction conversion type. However, being of the indirect conversion type is also acceptable.

For example, the X-ray detector 5 includes a Flat Panel Detector (FPD) that has a planar shape and is configured to accumulate electric charges converted from the X-rays that have passed through the patient P; and a gate driver configured to generate a drive pulse for reading the electric charges accumulated in the FPD. Generally speaking, the dimension of the FPD is in the range of 8 inches to 16 inches. The FPD is configured by two-dimensionally arranging small detecting elements in a column direction and a line direction. Each of the detecting elements includes: a photoelectric membrane configured to sense X-rays and to generate an electric charge in accordance with an incident X-ray amount; an electric charge accumulating capacitor configured to accumulate the electric charges occurring in the photoelectric membrane; and a Thin Film Transistor (TFT) configured to output the electric charges accumulated in the electric charge accumulating capacitor with predetermined timing. The accumulated electric charges are sequentially read according to the drive pulse supplied by the gate driver.

At a stage subsequent to the X-ray detector 5, projection data generating circuitry (not illustrated) is provided. The projection data generating circuitry includes a charge/voltage converter, an Analog/Digital (A/D) converter, and a parallel/serial converter. The charge/voltage converter is configured to convert the electric charges read from the FPD in parallel in units of lines or in units of columns, into voltage. The A/D converter is configured to convert the output from the charge/voltage converter into a digital signal. The parallel/serial converter is configured to convert a parallel signal resulting from a digital conversion, into a time-series serial signal. The projection data generating circuitry is configured to output the serial signal to the processing circuitry 26 as time-series projection data.

The table 7 has a mechanism capable of rising and reclining while the patient P is placed thereon and performing a position determining operation. The table 7 is provided with a state detector (not illustrated) configured to detect information about geometric arrangements such as the position of the table 7 itself. The state detector is configured to output the information about the geometric arrangements of the table 7 to the C-arm/table mechanism controlling unit 15.

The C-arm 9 is configured to hold the X-ray generating unit 3 and the X-ray detector 5 so as to oppose each other while the patient P and a tabletop of the table 7 are interposed therebetween. More specifically, the C-arm 9 is held by a holding unit (not illustrated) so as to be rotatable on an axis extending in an X-direction and being orthogonal to both a Z-direction perpendicular to the tabletop of the table 7 and a Y-direction along the long-axis direction of the tabletop. Further, the C-arm 9 has a substantially arc shape centered on an axis in the Y-direction and is held by the holding unit so as to be slidable along the substantially arc shape. Alternatively, the C-arm 9 may be configured to rotate on an axis extending in the X-direction, while using the holding unit as the center. The C-arm 9 is capable of acquiring X-ray images taken from various angular directions by combining the sliding and the rotation. The C-arm 9 is provided, in corresponding appropriate locations, with a plurality of power sources for realizing the sliding operation and the rotating operation.

Further, the C-arm 9 is provided with state detectors (not illustrated) configured to detect information about geometric arrangements such as an angle thereof and a posture and the position thereof. The state detectors are configured by using a position meter to detect a rotation angle and a moving amount, an encoder serving as a position detecting sensor, and/or the like, for example. As the encoder, it is possible to use a so-called absolute encoder of a magnetic type, a brush type, or a photoelectric type, for example. Further, as the state detectors, it is possible to use any of various types of position detecting mechanisms, as appropriate, such as a rotary encoder configured to output a rotation displacement as a digital signal or a linear encoder configured to output a linear displacement as a digital signal. These types of state detectors are configured to output the information about the geometric arrangements of the C-arm 9 to the C-arm/table mechanism controlling unit 15. In this situation, the information about the geometric arrangements of the C-arm 9 corresponds to information about geometric arrangements of the X-ray tube 3a and the X-ray detector 5.

The X-ray controller 11 is controlled by the system controlling unit 22. The X-ray controller 11 is configured to control the X-ray limiter 3b, an X-ray controlling unit 13a, and a high-voltage generator 13b.

The high-voltage generating unit 13 includes the X-ray controlling unit 13a and the high-voltage generator 13b.

The X-ray controlling unit 13a is configured to control an X-ray tube current, an X-ray tube voltage level, an application period, application timing, a repetition frequency, and the like of the high-voltage generator 13b, on the basis of an X-ray emission condition supplied from the X-ray controller 11.

The high-voltage generator 13b is controlled by the X-ray controller 11 and is configured to generate the high voltage to be applied to between the positive pole and the negative pole for accelerating the thermo electrons generated from the negative pole of the X-ray tube 3a and to apply the generated high voltage to the X-ray tube 3a.

The C-arm/table mechanism controlling unit 15 is controlled by the system controlling unit 22 and is configured to individually drive and control the C-arm 9 and the table 7. The C-arm/table mechanism controlling unit 15 is configured to write the information about the geometric arrangements of the C-arm 9 and the information about the geometric arrangements of the table 7 received from the state detectors (not illustrated), to the position data memory 21.

The position data memory 21 is configured to save the information about the geometric arrangements of the C-arm 9 and the information about the geometric arrangements of the table 7.

The system controlling unit 22 is a central processing unit configured to exercise control related to acquiring image data and to exercise control related to performing image processing processes, image playback processes, and the like on the acquired image data. For example, the system controlling unit 22 is configured to temporarily store therein information such as a command signal input through the input interface 23 and various types of initial setting conditions and to subsequently transmit these types of information to the X-ray controller 11, the C-arm/table mechanism controlling unit 15, and/or the processing circuitry 26.

The input interface 23 is configured to receive inputs of patient information, settings of X-ray image taking conditions including the X-ray emission condition, inputs of various types of command signals, and the like. For example, the input interface 23 is realized by using a trackball, a switch button, a mouse, a keyboard, a touchpad on which input operations can be performed by touching an operation surface thereof, a touch panel display in which a display screen and a touchpad are integrally formed, and/or the like which are used for instructing to move the C-arm 9, for setting a Region Of Interest (ROI), and the like.

The input interface 23 is connected to the system controlling unit 22. The input interface 23 is configured to convert input operations received from the user into electrical signals and to output the electrical signals to the system controlling unit 22. In the present disclosure, the input interface 23 does not necessarily need to include physical operation component parts such as the mouse, the keyboard, and/or the like. For instance, possible examples of the input interface 23 include electrical signal processing circuitry configured to receive an electrical signal corresponding to an input operation from an external input device provided separately from the apparatus and to output the electrical signal to the system controlling unit 22. The input interface 23 corresponds to an input unit.

The display 24 is structured with a display main body configured to display medical images and the like, internal circuitry configured to supply display-purpose signals to the display main body, and peripheral circuitry such as a connector or a cable connecting the display main body to the internal circuitry. The internal circuitry is configured to generate display data by multiplexing additional information onto image data supplied from the processing circuitry 26. The additional information may be, for example, patient information, a projection data generating condition, and/or the like. The internal circuitry is configured to perform a D/A conversion and a TV format conversion on the generated display data so as to display an image corresponding to the display data on the display main body. The display 24 corresponds to a display unit.

The memory 25 includes a memory main body such as a Read Only Memory (ROM), a Random Access Memory (RAM), a Hardware Disk Drive (HDD), or an image memory configured to record therein electric information; and peripheral circuitry such as a memory controller or a memory interface accompanying the memory main body. For example, the memory 25 has stored therein a plurality of programs executed by the processing circuitry 26, X-ray images generated by the processing circuitry 26, data used in various types of processes performed by the processing circuitry 26, data that are currently processed, and data resulting from processes, and the like. The data used in the processes performed by the processing circuitry 26 may include, for example, anatomical information related to an imaged site of an X-ray image. For example, each of the plurality of programs executed by the processing circuitry 26 corresponds to a different one of the following: an image computing function 26a, a display data generating function 26b, the region setting function 26c, a registration function 26d, a matching degree calculating function 26e, and a determining function 26f.

The processing circuitry 26 is a processor configured to realize the image computing function 26a, the display data generating function 26b, the region setting function 26c, the registration function 26d, the matching degree calculating function 26e, and the determining function 26f corresponding to the programs, by reading and executing the programs saved in the memory 25. Further, the X-ray controller 11, the C-arm/table mechanism controlling unit 15, and the system controlling unit 22 illustrated in FIG. 1 are also similarly realized by one or more processors configured to execute the programs corresponding to the various types of functions implemented by these units.

In this situation, the term "processor" denotes, for example, a Central Processing Unit (CPU), a Graphics Processing Unit (GPU), or circuitry such as an Application Specific Integrated Circuit (ASIC) or a programmable logic device (e.g., a Simple Programmable Logic Device (SPLD), a Complex Programmable Logic Device (CPLD), or a Field Programmable Gate Array (FPGA)).

Alternatively, instead of having the programs saved in the memory 25, it is also acceptable to directly incorporate the programs in the circuit of one or more processors. In that situation, the one or more processors realize the functions by reading and executing the programs incorporated in the circuit thereof. Further, although FIG. 1 illustrates the example in which the single processing circuit (i.e., the processing circuitry 26) realizes the image computing function 26a, the display data generating function 26b, the region setting function 26c, the registration function 26d, the matching degree calculating function 26e, and the determining function 26f, possible embodiments are not limited to this example. It is also acceptable to structure a processing circuit by combining together a plurality of independent processors, so that the functions are realized as a result of the processors executing the programs.

The processing circuitry 26 includes the image computing function 26a, the display data generating function 26b, and the region setting function 26c. The image computing function 26a includes the registration function 26d, the matching degree calculating function 26e, and the determining function 26f. The processing circuitry 26 realizing the image computing function 26a may be realized with image computing circuitry. The processing circuitry 26 or the image computing circuitry realizing the image computing function 26a corresponds to an image computing unit. Further, the processing circuitry 26 realizing the display data generating function 26b may be realized by display data generating circuitry. The processing circuitry 26 or the display data generating circuitry realizing the display data generating function 26b corresponds to a display data generating unit. The processing circuitry 26 realizing the region setting function 26c corresponds to a region setting unit.

By employing the image computing function 26a, the processing circuitry 26 is configured to sequentially save, into projection data storage circuitry (not illustrated), the time-series projection data output from the projection data generating circuitry of the X-ray detector 5. On the basis of the time-series projection data, the image computing function 26a is configured to generate the X-ray images derived from two-dimensional projection data. The image computing function 26a is configured to save the generated X-ray images into the memory 25.

Examples of the X-ray images which the image computing function 26a is capable of generating include mask images (non-contrast enhanced images) and contrast images (contrast enhanced images). The mask images are X-ray images generated by performing an X-ray imaging process on the patient P before a contrast agent is administered and are projection images including bone images. The contrast images are X-ray images generated after the contrast agent is administered by performing an X-ray imaging process on the patient P and are projection images including bone and blood vessel images. A mask image is generated for each X-ray emission condition. In other words, a plurality of mask images are generated at a predetermined frame rate corresponding to the number of times of X-ray emissions per second. Also, a plurality of contrast images are similarly generated at the predetermined frame rate.

Further, by employing the image computing function 26a, the processing circuitry 26 may generate three-dimensional (3D) image data by performing a predetermined reconstructing process on projection data that was acquired by continuously rotating the X-ray tube 3a and the X-ray detector 5 around the patient P and was saved in the memory 25. The image computing function 26a is configured to save the generated 3D image data into the memory 25.

By employing the display data generating function 26b, the processing circuitry 26 is configured to generate display data including the X-ray images generated by the image computing function 26a. The display data generating function 26b is configured to send the display data to the display 24.

By employing the region setting function 26c, the processing circuitry 26 is configured set a region of interest in the X-ray images. For example, the region setting function 26c may set the region of interest on the basis of anatomical information related to the imaged site in the X-ray images. The anatomical information may include information about the imaged site and the information about the geometric arrangements of the X-ray tube 3a and the X-ray detector 5. For example, the region setting function 26c may estimate the position of a field of view on the basis of the information about the imaged site in an examination protocol obtained from the system controlling unit 22 and the angle and the position of the C-arm 9 obtained from the system controlling unit 22, so as to set the region of interest on the basis of the position of the field of view. Further, in addition to the information about the geometric arrangements of the X-ray tube 3a and the X-ray detector 5, the region setting function 26c may set the region of interest, by using the position of the table 7, a Source-Image Distance (SID), a Field of View (FOV), patient information (height/weight), patient posture information, and/or the like.

By employing the registration function 26d, the processing circuitry 26 is configured to perform registration between one contrast image among a plurality of contrast images and each of the plurality of mask images. For example, the one contrast image is a contrast image selected from among the plurality of contrast images displayed on the display 24, according to a user instruction received via the input interface 23. The processing circuitry 26 realizing the registration function 26d corresponds to a registration unit.

For example, the registration function 26d is configured to perform the registration by applying at least one transformation selected from between translation and rotation to the plurality of mask images, on the basis of the one contrast image and each of the plurality of mask images. In this situation, the registration function 26d may perform the registration on each of the plurality of contrast images. In other words, the registration function 26d may perform the registration between all the contrast images and the plurality of mask images.

By employing the matching degree calculating function 26e, the processing circuitry 26 is configured to calculate a plurality of matching degrees between the plurality of mask images and the one contrast image registered with each other, on the basis of the plurality of mask images and the one contrast image registered with each other. The matching degrees are indices indicating degrees of matching between the plurality of mask images and the one contrast image registered with each other. In other words, the matching degrees correspond to the indices (e.g., levels of similarity) indicating degrees of similarity between the plurality of mask images and the one contrast image registered with each other. The processing circuitry 26 realizing the matching degree calculating function 26e corresponds to a matching degree calculating unit.

More specifically, by employing the matching degree calculating function 26e, the processing circuitry 26 is configured to calculate a plurality of images (hereinafter, "difference images") by calculating the differences between each of the plurality of mask images and the one contrast image registered with each other, with respect to the total number of the registered plurality of mask images. In the following sections, to explain a specific example, the total number of the plurality of contrast images respectively corresponding to the plurality of frames is assumed to be n (where n is a natural number of 2 or larger). Further, one contrast image $C_j$ selected by the user is assumed to be a j-th frame. Furthermore, the total number of the registered plurality of mask images M is assumed to be m (where m is a natural number of 2 or larger). Also, a mask image corresponding to an i-th frame (where $1 \leq i \leq m$) and having been registered will be expressed as $M_i$.

Among the plurality of difference images, a difference image $D_i$ (where $1 \leq i \leq m$) corresponding to the i-th frame is calculated as $M_i - C_j$. By employing the matching degree calculating function 26e, the processing circuitry 26 is configured to calculate the matching degrees by using a plurality of pixel values from each of the plurality of difference images. For example, the matching degree corresponds to a variance value or a standard deviation value of each of the plurality of difference images $D_i$. However, the matching degrees do not necessarily have to be variance values or standard deviation values. As long as similarities between each of the plurality of mask images $M_i$ and the contrast image $C_j$ registered with each other are indicated, it is acceptable to perform the calculation by using any of known methods. In the following sections, to explain a specific example, it will be assumed that the matching degrees are variance values. In this situation, a maximum matching degree corresponds to a minimum variance value. The matching degree calculating function 26e is configured to store the plurality of matching degrees and the plurality of difference images resulting from the calculations into the memory 25, so as to be kept in association with each other.

In an example, by employing the matching degree calculating function 26e, the processing circuitry 26 may calculate an average difference image $D_{ave}$, by calculating the difference between an average image $(M_{ave}=1/m \times \Sigma_{i=1}^{m} (M_i))$ of the registered mask images and the one contrast image $C_j$ selected by the user. Subsequently, the matching degree calculating function 26e may calculate an average matching degree by using the average difference image $D_{ave}$. In this situation, the average matching degree is included in the plurality of matching degrees. Further, in the situation where the registration is performed between all the contrast images and the plurality of mask images, the matching degree calculating function 26e is configured to calculate a plurality of matching degrees corresponding to combinations of the plurality of mask images and the plurality of contrast images registered with each other.

Figure 2:
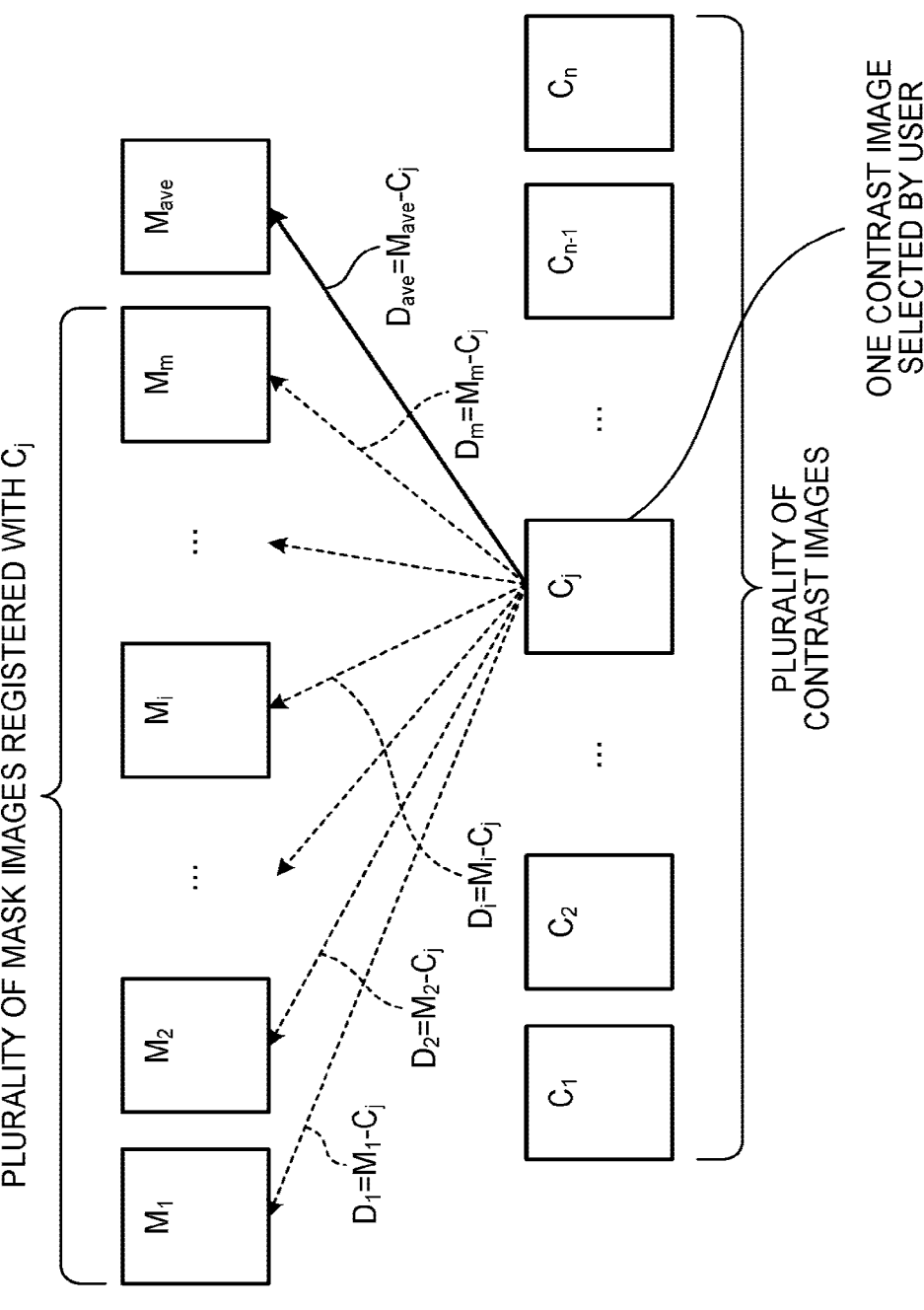
FIG. 2 is a drawing according to the embodiment illustrating an example of a matching degree calculating process.

FIG. 2 is a drawing illustrating an example of the matching degree calculating process. As illustrated in FIG. 2, by employing the matching degree calculating function 26e, the processing circuitry 26 is configured to calculate m difference images $D_i$ $(=M_i-C_j)$, by calculating the difference between the one contrast image $C_j$ selected by the user and the registered plurality of mask images $M_i$, with respect to the total number m. Alternatively, the matching degree calculating function 26e may calculate a difference image $D_{ave}$ $(=M_{ave} C_j)$ between the one contrast image $C_j$ selected by the user and the average mask image $M_{ave}$ of the registered plurality of mask images.

By employing the determining function 26f, the processing circuitry 26 is configured to determine the difference between one of the mask images corresponding to a maximum matching degree among the plurality of matching degrees and the one contrast image, as one subtraction image corresponding to the one contrast image. The processing circuitry 26 realizing the determining function 26f corresponds to a determining unit. Further, the determining function 26f is configured to determine the differences between a predetermined number of the plurality of mask images having higher matching degrees among the plurality of matching degrees and the one contrast image, as a plurality of subtraction images including the one subtraction image corresponding to the one contrast image. In this situation, the predetermined number is a natural number of 2 or larger set in advance. In the following sections, to explain a specific example, the predetermined number will be assumed to be 3.

More specifically, by employing the determining function 26f, the processing circuitry 26 is configured to identify the maximum matching degree among the plurality of matching degrees. The determining function 26f is configured to read the difference image corresponding to the maximum matching degree from the memory 25 and to determine the read difference image as the one subtraction image corresponding to the one contrast image. The one subtraction image corresponds to a DSA image related to the one contrast image. Alternatively, the determining function 26f may identify a predetermined number of (e.g., three) matching degrees in descending order starting with the maximum matching degree. In that situation, the determining function 26f is configured to read the predetermined number of difference images corresponding to the identified predetermined number of matching degrees from the memory 25 and to determine the read predetermined number of difference images as three subtraction images corresponding to the one contrast image.

By employing the display data generating function 26b, the processing circuitry 26 is configured to generate a plurality of display-purpose subtraction images, on the basis of the determined plurality of subtraction images. The display 24 is configured to display the generated plurality of subtraction images.

An overall configuration of the X-ray diagnosis apparatus 1 according to the embodiment has thus been explained. The X-ray diagnosis apparatus 1 according to the embodiment structured as described above is configured to perform a process (hereinafter, "DSA image determining process") of determining the subtraction image (a DSA image) corresponding to the one contrast image designated by the user and causing the display 24 to display the determined subtraction image. In the following sections, a procedure in the DSA image determining process will be explained, with reference to FIG. 3. FIG. 3 is a flowchart illustrating an example of the procedure in the DSA image determining process. DSA Image Determining Process Step S301:

The system controlling unit 22 performs an imaging process (hereinafter, "mask imaging process") at the predetermined frame rate on the patient P before a contrast agent is administered. By employing the image computing function 26a, the processing circuitry 26 generates the plurality of mask images in a time series, on the basis of the plurality of pieces of time-series projection data generated in the mask imaging process. The image computing function 26a stores the plurality of mask images into the memory 25. In this situation, the plurality of mask images may be displayed on the display 24.

Step S302:

The system controlling unit 22 performs an imaging process (hereinafter, "contrast imaging process") at a predetermined frame rate on the patient P, after a contrast agent is administered. By employing the image computing function 26a, the processing circuitry 26 generates a plurality of contrast images in a time series, on the basis of the plurality of pieces of time-series projection data generated in the contrast imaging process. The image computing function 26a stores the plurality of contrast images into the memory 25. By employing the display data generating function 26b, the processing circuitry 26 generates a plurality of display-purpose contrast images on the basis of the plurality of contrast images. The display 24 displays the plurality of display-purpose contrast images.

Step S303:

The input interface 23 receives an input of a user instruction to select one contrast image from among the displayed plurality of contrast images. In other words, according to the user instruction, the one contrast image is selected from among the plurality of contrast images.

Step S304:

By employing the registration function 26d, the processing circuitry 26 performs registration between the one contrast image selected from among the plurality of contrast images and each of the plurality of mask images. More specifically, with respect to each of the plurality of mask images, the registration function 26d calculates a deviation amount from the one contrast image. Subsequently, with respect to each of the plurality of mask images, the registration function 26d calculates a translation amount and a rotation amount of the specific mask image, by using the calculated deviation amounts. By transforming each of the plurality of mask images by using the translation amount and the rotation amount corresponding to the mask image, the registration function 26d performs the registration with the one contrast image. The transformation performed on the mask images based on the calculated deviation amounts may be realized with an affine transformation performed on a plurality of pixels in the mask images, for example. However, possible transformations are not limited to the affine transformation.

Step S305:

By employing the matching degree calculating function 26*e*, the processing circuitry 26 calculates a plurality of matching degrees corresponding to the total number of the plurality of mask images, on the basis of the plurality of mask images and the one contrast image registered with each other. More specifically, the matching degree calculating function 26*e* generates a plurality of difference images corresponding to the total number of the plurality of mask images, by calculating the difference between each of the plurality of mask images and the one contrast image registered with each other. Subsequently, the matching degree calculating function 26*e* calculates the plurality of matching degrees respectively corresponding to the plurality of difference images, on the basis of each of the plurality of difference images.

Step S306:

By employing the determining function 26*f*, the processing circuitry 26 determines one of the difference images corresponding to the maximum matching degree among the plurality of matching degrees, as one subtraction image corresponding to the one selected contrast image. More specifically, the determining function 26*f* determines three difference images having higher matching degrees, as the plurality of subtraction images.

Step S307:

By employing the display data generating function 26*b*, the processing circuitry 26 generates a plurality of display-purpose subtraction images, on the basis of the determined plurality of subtraction images. The display 24 displays the generated plurality of subtraction images arranged as appropriate. In this situation, the display 24 may display either the average difference image $D_{ave}$ or a difference image $D_1$ obtained by using the registered mask image in the first frame, together with the plurality of subtraction images.

Figure 4:
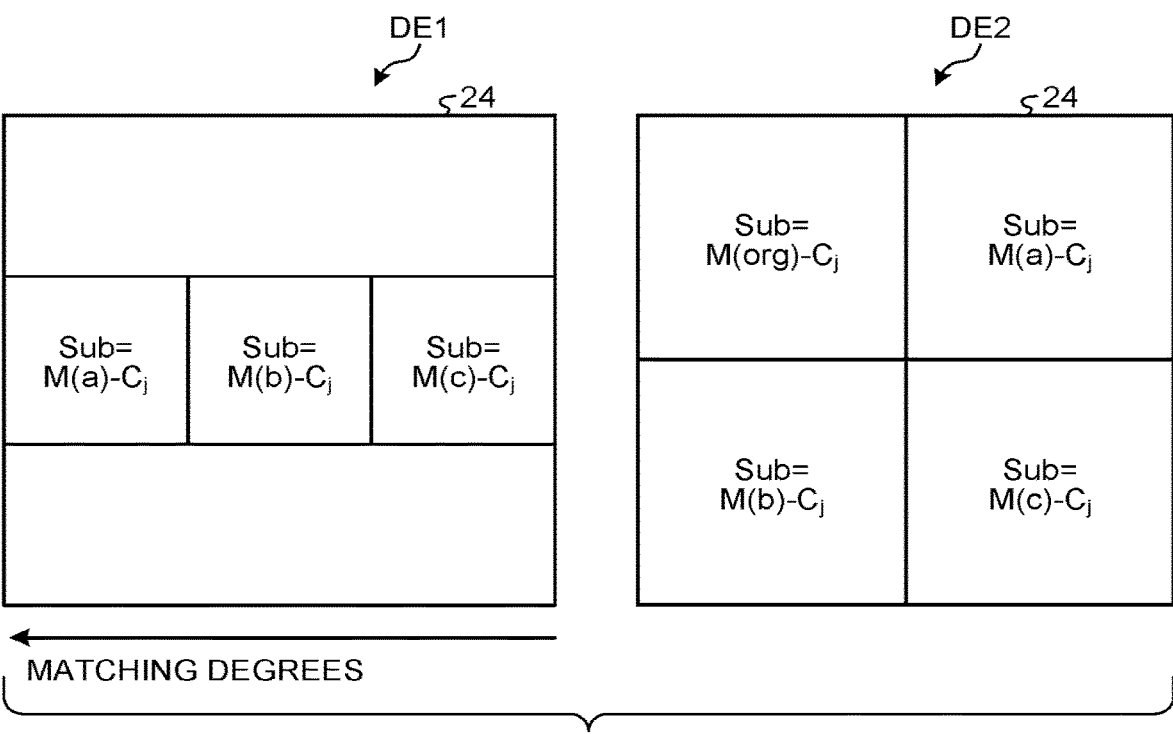
FIG. 4 is a drawing according to the embodiment illustrating display examples of a plurality of subtraction images displayed on a display.

FIG. 4 is a drawing illustrating display examples of a plurality of subtraction images Sub displayed on the display 24 at step S307. In FIG. 4, M(a), M(b), and M(c) denote mask images having higher matching degrees (levels of similarity). Further, in FIG. 4, M(org) denotes an original mask image which may be, for example, the mask image in the first frame or the average mask image $M_{ave}$. In FIG. 4, DE1 denotes a display example in which the three types of subtraction images Sub having the higher matching degrees (levels of similarity) are displayed side by side in a display region of the display 24. In FIG. 4, DE2 denotes another display example in which the three types of subtraction images Sub having the higher matching degrees (levels of similarity) are displayed together with a subtraction image calculated by using the registered original mask image M(org), while being arranged in the display region of the display 24.

Step S308:

From among the displayed plurality of subtraction images, when one subtraction image is selected according to a user instruction received via the input interface 23, the processing circuitry 26 stores the selected subtraction image into the memory 25 as a DSA image. Thus, the DSA image determining process ends.

The X-ray diagnosis apparatus 1 according to the embodiment described above is configured: to perform the registration between the one contrast image and each of the plurality of mask images; to calculate the plurality of matching degrees between the plurality of mask images and the one contrast image registered with each other, on the basis of the plurality of mask images and the one contrast image registered with each other; and to determine the difference (the difference image) between the one of the mask images corresponding to the maximum matching degree among the plurality of matching degrees and the one contrast image, as the one subtraction image corresponding to the one contrast image. Further, the X-ray diagnosis apparatus 1 in the present example is configured to perform the registration, by applying at least one transformation selected from between translation and rotation to the plurality of mask images, on the basis of the one contrast image and each of the plurality of mask images. Further, the X-ray diagnosis apparatus 1 is configured to determine the differences (the difference images) between the predetermined number of the plurality of mask images having higher matching degrees among the plurality of matching degrees and the one contrast image, as the plurality of subtraction images including the one subtraction image and to display the plurality of subtraction images.

With these arrangements, the X-ray diagnosis apparatus 1 according to the embodiment is configured to determine the plurality of subtraction images having higher matching degrees in accordance with the selection of the contrast image made by the user and to cause the display 24 to display the plurality of subtraction images as candidates for a DSA image. Because the X-ray diagnosis apparatus 1 is capable of determining the DSA image on the basis of the selection of the contrast image and the selection of the subtraction images, it is possible to shorten work time of the user. Consequently, the X-ray diagnosis apparatus 1 is able to improve a throughput of the processes related to determining and selecting the DSA image and to thus reduce burdens that may be imposed on operations performed by the user.

Further, the X-ray diagnosis apparatus 1 according to the embodiment is configured to perform the registration by applying the transformation to the mask images in accordance with the deviations between the contrast image and the mask images and to calculate the matching degrees on the basis of the subtraction images of which the deviations are decreased to the minimum level. Accordingly, it is possible to enhance image quality of the plurality of subtraction images including the subtraction image related to the maximum matching degree, compared to conventional examples.

As explained above, the X-ray diagnosis apparatus 1 is capable of determining an excellent DSA image having little misregistration while the burdens on user operations are reduced and is thus able to improve efficiency in diagnosing processes for the patient P and to improve a throughput of medical examinations.

First Modification Example

In the present modification example, two mask images corresponding to the frames preceding and following the mask image corresponding to the maximum matching degree are used for determining the differences between the two mask images and the one contrast image as two subtraction images related to the two mask images in the preceding and following frames, so as to display the one subtraction image related to the maximum matching degree and the two determined subtraction images. In the present modification example, the plurality of mask images are a series of mask images generated at a predetermined frame rate. In the following sections, the present modification example will be explained on the assumption that the preceding and following frames are each a single frame; however, the preceding and following frames do not each necessarily have to be a single frame, and two or more frames may precede and follow.

By employing the determining function 26f, the processing circuitry 26 is configured to determine the differences (difference images) between the two mask images corresponding to the frames preceding and following the maximum matching degree and the one contrast image, as two subtraction images related to the two mask images in the preceding and following frames. The two mask images are the mask images on which the registration was performed by the registration function 26d. The process performed by the determining function 26f is carried out at step S306 in FIG. 3 included in the DSA image determining process.

The display 24 is configured to display the one subtraction image corresponding to the maximum matching degree and the two determined subtraction images. The process performed by the display 24 is carried out at step S307 in FIG. 3 included in the DSA image determining process.

Figure 5:
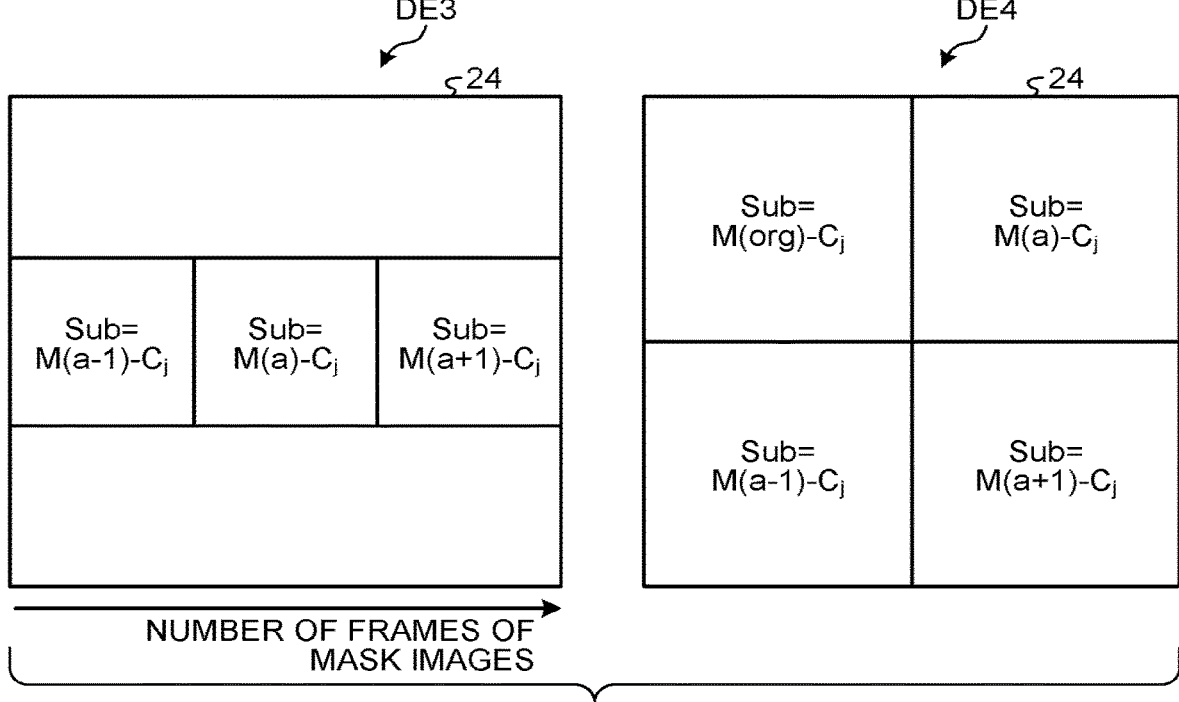
FIG. 5 is a drawing according to a first modification example of the embodiment illustrating display examples of a plurality of subtraction images displayed on the display.

FIG. 5 is a drawing illustrating display examples of a plurality of subtraction images Sub displayed on the display 24. In FIG. 5, M(a) denotes a mask image corresponding to the maximum matching degree. In FIG. 5, M(a−1) denotes a mask image corresponding to the frame preceding the frame of the mask image related to the maximum matching degree. In FIG. 5, M(a+1) denotes a mask image corresponding to the frame following the frame of the mask image related to the maximum matching degree.

In FIG. 5, DE3 denotes a display example in which three types of subtraction images Sub are displayed side by side in a display region of the display 24, in the order of the frames of the mask images, while the subtraction image related to the maximum matching degrees is placed at the center. In FIG. 5, DE4 denotes a display example in which the subtraction image Sub related to the maximum matching degree and the two subtraction images Sub obtained by using the two mask images in the frames preceding and following the mask image related to the maximum matching degree are displayed, together with the subtraction image calculated by using the original mask image M(org), while being arranged in the display region of the display 24. The user will select a DSA image from among the displayed plurality of subtraction images, via the input interface 23.

While the plurality of mask images are the series of mask images generated at the predetermined frame rate, the X-ray diagnosis apparatus 1 according to the present modification example is configured to determine the differences (the difference images) between the two mask images corresponding to the frames preceding and following the maximum matching degree and the one contrast image, as the two subtraction images related to the two mask images, so as to display the one subtraction image and the two subtraction images. With this arrangement, according to the present modification example, with respect to the maximum matching degree, it is possible to display, on the display 24, the plurality of subtraction images related to the frames preceding and following the mask image related to the maximum matching degree. Consequently, the X-ray diagnosis apparatus 1 is able to present the user with the candidates for the subtraction image having little misregistration. Because the other advantageous effects are the same as those of the embodiment, explanations thereof will be omitted.

Second Modification Example

In a second modification example, difference images corresponding to the differences between two contrast images in the preceding and following frames of the one contrast image selected by the user from among the plurality of contrast images and two mask images having the maximum matching degrees with respect to the two contrast images are determined as two subtraction images related to the two contrast images, so as to display the one subtraction image related to the maximum matching degree and the two determined subtraction images.

By employing the registration function 26d, the processing circuitry 26 is configured to perform registration between the two contrast images corresponding to the frames preceding and following the one contrast image selected by the user and the plurality of mask images. The process performed by the registration function 26d is carried out at step S304 in FIG. 3 included in the DSA image determining process.

By employing the matching degree calculating function 26e, the processing circuitry 26 is configured to calculate a plurality of matching degrees between the plurality of mask images and the two contrast images registered with each other, on the basis of the plurality of mask images and the two contrast images registered with each other. In other words, the matching degree calculating function 26e is configured to calculate the plurality of matching degrees on the basis of a plurality of difference images corresponding to the differences between the plurality of mask images and the two contrast images registered with each other. The process performed by the matching degree calculating function 26e is carried out at step S305 in FIG. 3 included in the DSA image determining process.

By employing the determining function 26f, the processing circuitry 26 is configured to determine the differences between the two contrast images and the two mask image respectively corresponding to the maximum matching degrees related to the two contrast images, as the two subtraction images related to the two contrast images in the preceding and following frames. In other words, with respect to each of the two contrast images, the determining function 26f is configured to determine the difference image corresponding to the maximum matching degree among the plurality of matching degrees as a subtraction image. The process performed by the determining function 26f is carried out at step S306 in FIG. 3 included in the DSA image determining process.

The display 24 is configured to display the one subtraction image corresponding to the maximum matching degree and the two determined subtraction images described above. The process performed by the display 24 is carried out at step S307 in FIG. 3 included in the DSA image determining process.

Figure 6:
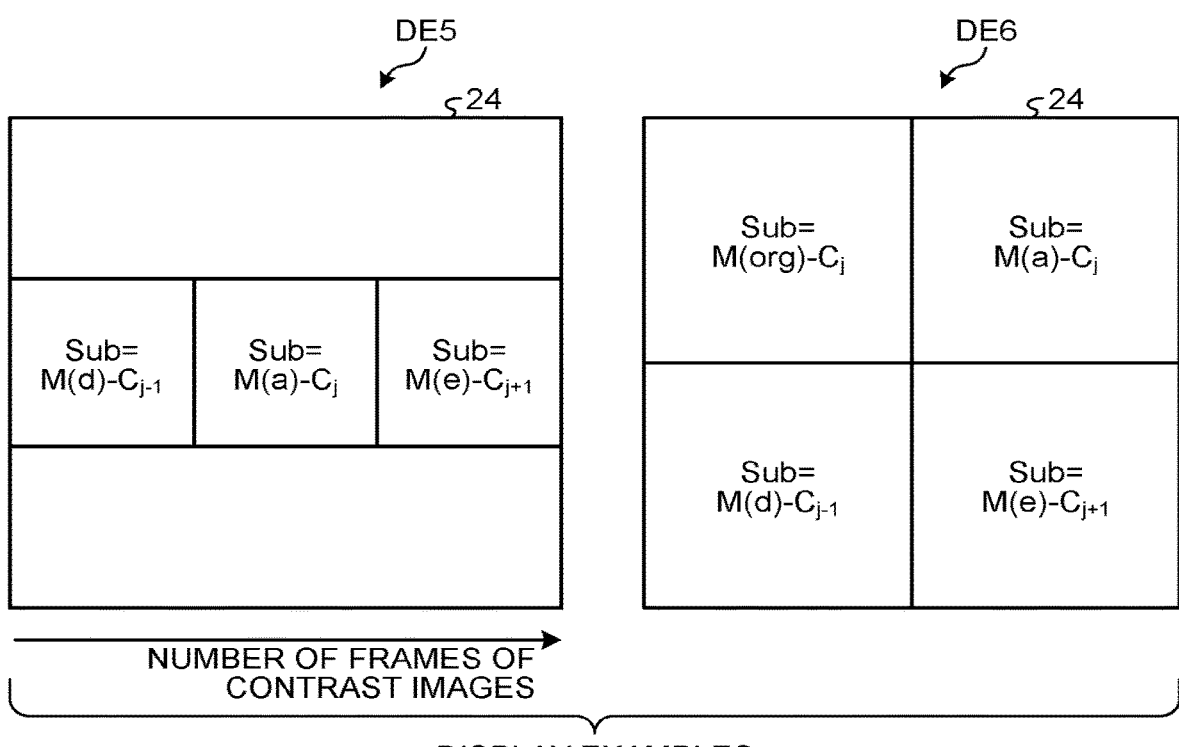
FIG. 6 is a drawing according to a second modification example of the embodiment illustrating display examples of a plurality of subtraction images displayed on the display.

FIG. 6 is a drawing illustrating display examples of a plurality of subtraction images Sub displayed on the display 24. In FIG. 6, M(a) denotes a mask image related to the maximum matching degree, with respect to the one contrast image $C_j$ selected by the user. In FIG. 6, M(d) denotes a mask image related to the maximum matching degree with respect to a contrast image $C_{j-1}$ in the frame preceding the one contrast image $C_j$ selected by the user. In FIG. 6, M(e) denotes a mask image related to the maximum matching degree with respect to a contrast image $C_{j+1}$ in the frame following the contrast image $C_j$.

In FIG. 6, DE5 denotes a display example in which three types of subtraction images Sub are displayed side by side in a display region of the display 24, in the order of the frames of the contrast images, while the subtraction image related to the contrast image $C_j$ selected by the user is placed at the center. In FIG. 6, DE6 denotes a display example in which the subtraction image Sub related to the contrast image $C_j$ and the two subtraction images Sub related to the two contrast images $C_{j-1}$ and $C_{j+1}$ in the preceding and following frames are displayed, together with the subtraction image calculated by using the original mask image M(org), while being arranged in the display region of the display 24. The user will select a DSA image from among the displayed plurality of subtraction images, via the input interface 23.

The X-ray diagnosis apparatus 1 according to the present modification example is configured: to perform the registration between the two contrast images corresponding to the frames preceding and following the one contrast image and the plurality of mask images; to calculate the plurality of matching degrees between the plurality of mask images and the two contrast images registered with each other, on the basis of the plurality of mask images and the two contrast images registered with each other; to determine the differences between the two contrast images and the two mask images respectively corresponding to the maximum matching degrees related to the two contrast images, as the two subtraction images related to the two contrast images in the preceding and following frames; and to display the one subtraction image and the two subtraction images.

With this arrangement, the X-ray diagnosis apparatus 1 according to the present modification example is capable of causing the display 24 to display, with respect to the maximum matching degree, the plurality of subtraction images related to the frames preceding and following the contrast image selected by the user. Consequently, the X-ray diagnosis apparatus 1 is able to present the user with the candidates for the subtraction image that are adjacent (close) to the frame of the contrast image selected by the user and that have little misregistration. Because the other advantageous effects are the same as those of the embodiment, explanations thereof will be omitted.

Third Modification Example

A third modification example corresponds to a combination of the embodiment and the second modification example. More specifically, the processes in the present modification example further include the following processes, in addition to the processes in the second modification example.

By employing the determining function 26f, the processing circuitry 26 is configured to further determine the differences between a predetermined number of the plurality of mask images having higher matching degrees among the plurality of matching degrees and the one contrast image selected by the user and the two contrast images corresponding to the frames preceding and following the one contrast image, as a plurality of subtraction images. In other words, with respect to each of the two contrast images corresponding to the preceding and following frames, the determining function 26f is configured to determine a difference image corresponding to the maximum matching degree among the plurality of matching degrees as a subtraction image. In the present modification example, the predetermined number is assumed to be three. The process performed by the determining function 26f is carried out at step S306 in FIG. 3 included in the DSA image determining process.

The display 24 is configured to display the one subtraction image corresponding to the maximum matching degree with respect to the one contrast image selected by the user, the two subtraction images related to the two contrast images in the preceding and following frames, and the plurality of subtraction images described above. The process performed by the display 24 is carried out at step S307 in FIG. 3 included in the DSA image determining process.

Figure 7:
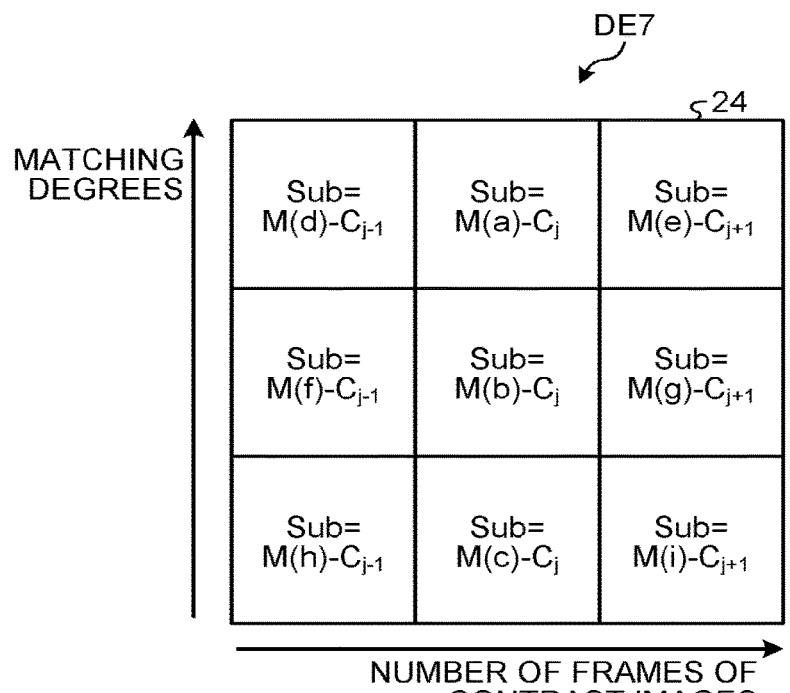
FIG. 7 is a drawing according to a third modification example of the embodiment illustrating a display example of a plurality of subtraction images displayed on the display.

FIG. 7 is a drawing illustrating a display example DE7 of a plurality of subtraction images Sub displayed on the display 24. In FIG. 7, M(a) denotes a mask image related to the maximum matching degree with respect to the one contrast image $C_j$ selected by the user. In FIG. 7, M(a), M(b), and M(c) denote mask images having higher matching degrees (levels of similarity) with respect to the contrast image $C_j$. Further, in FIG. 7, M(d) denotes a mask image related to the maximum matching degree with respect to the contrast image in the frame preceding the one contrast image $C_j$ selected by the user.

In FIG. 7, M(d), M(f), and M(h) denote mask images having higher matching degrees (levels of similarity) with respect to the contrast image $C_{j-1}$. In FIG. 7, M(e) denotes a mask image related to the maximum matching degree with respect to the contrast image $C_{j+1}$ in the frame following the contrast image $C_j$. In FIG. 7, M(e), M(g), and M(i) denote mask images having higher matching degrees (levels of similarity) with respect to the contrast image $C_{j+1}$. The user will select a DSA image from among the plurality of subtraction images displayed in DE7, via the input interface 23.

The X-ray diagnosis apparatus 1 according to the present modification example is configured: to further determine the differences between the predetermined number of the plurality of mask images having higher matching degrees among the plurality of matching degrees and the one contrast image and the two contrast images, as the plurality of subtraction images; and to display the one subtraction image determined in the embodiment, the two subtraction images determined in the second modification example, and the plurality of subtraction images. Because advantageous effects of the present modification example correspond to the advantageous effects of the embodiment and the advantageous effects of the second modification example, explanations thereof will be omitted.

Fourth Modification Example

A fourth modification example corresponds to a combination of the first modification example and the second modification example. The plurality of mask images in the present modification example are a series of mask images generated at a predetermined frame rate. More specifically, the processes in the present modification example further include the following processes in addition to the processes in the second modification example.

By employing the determining function 26f, the processing circuitry 26 is configured to determine the differences between the plurality of mask images corresponding to the frames preceding and following the maximum matching degrees related to the two contrast images in the frames preceding and following the one contrast image selected by the user and the two contrast images, as a plurality of subtraction images related to the two mask images in the preceding and following frames. In other words, with respect to each of the two mask images corresponding to the preceding and following frames, the determining function 26f is configured to determine the difference image corresponding to the maximum matching degree among the plurality of matching degrees, as the subtraction image. The process performed by the determining function 26f is carried out at step S306 in FIG. 3 included in the DSA image determining process.

The display 24 is configured to display the one subtraction image corresponding to the maximum matching degree with respect to the one contrast image selected by the user, the two subtraction image related to the two contrast images in the frames preceding and following the one contrast image, and the determined plurality of subtraction images. The process performed by the display 24 is carried out at step S307 in FIG. 3 included in the DSA image determining process.

Figure 8:
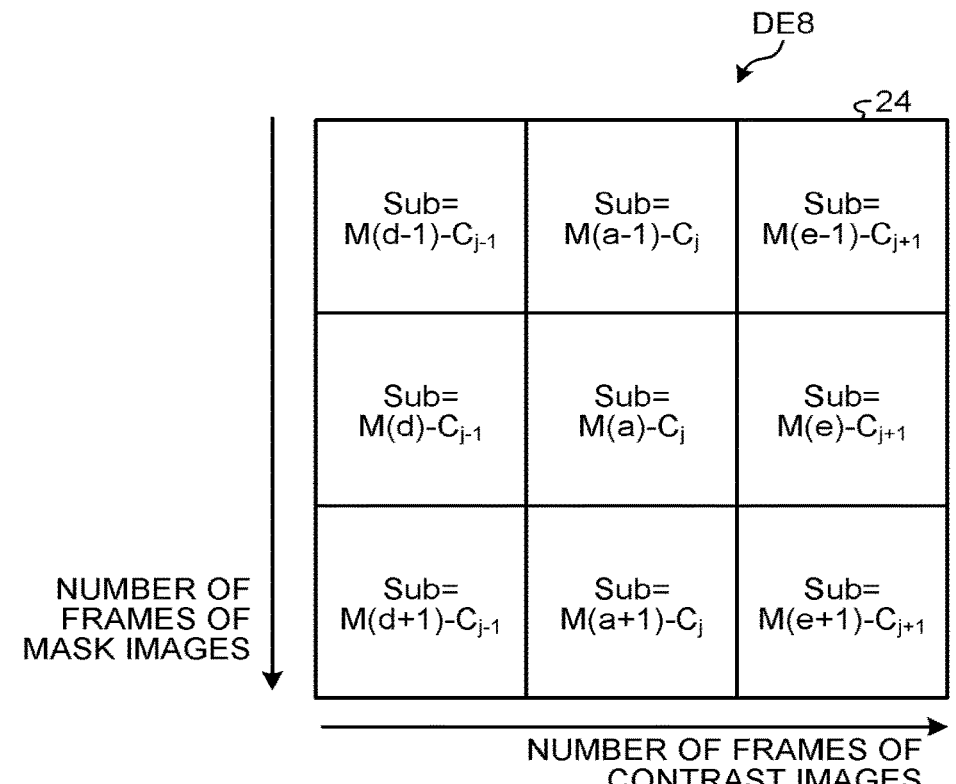
FIG. 8 is a drawing according to a fourth modification example of the embodiment illustrating a display example of a plurality of subtraction images displayed on the display.

FIG. 8 is a drawing illustrating a display example DE8 of a plurality of subtraction images Sub displayed on the display 24. In FIG. 8, M(a) denotes a mask image related to the maximum matching degree with respect to the one contrast image $C_j$ selected by the user. In FIG. 8, M(a−1) and M(a+1) respectively correspond to the two mask images in the frames preceding and following the mask image M(a). In FIG. 8, M(d) denotes a mask image related to the maximum matching degree with respect to the contrast image $C_{j-1}$ in the frame preceding the one contrast image $C_j$ selected by the user. In FIG. 8, M(d−1) and M(d+1) respectively correspond to the two mask images in the frames preceding and following the mask image M(d). Further, in FIG. 8, M(e) denotes a mask image related to the maximum matching degree with respect to the contrast image $C_{j+1}$ in the frame following the one contrast image $C_j$ selected by the user. In FIG. 8, M(e−1) and M(e+1) respectively correspond to the two mask images in the frames preceding and following the mask image M(e). The user will select a DSA image from among the plurality of subtraction images displayed in DE8, via the input interface 23.

While the plurality of mask images are the series of mask images generated at the predetermined frame rate, the X-ray diagnosis apparatus 1 according to the present modification example is configured: to determine the differences between the plurality of mask images corresponding to the frames preceding and following the maximum matching degree with respect to the two contrast images and the two contrast images, as the plurality of subtraction images related to the two mask images in the preceding and following frames; and to display the one subtraction image determined in the embodiment, the two subtraction images determined in the second modification example, and the plurality of subtraction images described above. Because advantageous effects of the present modification example correspond to the advantageous effects of the first modification example and the advantageous effects of the second modification example, explanations thereof will be omitted.

Fifth Modification Example

In the present modification example, the DSA image determining process is applied to each of a plurality of regions of interest set in the one contrast image selected by the user. The plurality of regions of interest are set in advance on the basis of X-ray image taking conditions (e.g., the imaged site, a lesion site, a lesion name, etc.) or the like. Alternatively, the plurality of regions of interest may be set by the region setting function 26c according to a user instruction received via the input interface 23.

By employing the region setting function 26c, the processing circuitry 26 is configured to set the plurality of regions of interest on the basis of the X-ray image taking conditions for the patient P. The process performed by the region setting function 26c is carried out at an arbitrary stage prior to step S303 in FIG. 3 included in the DSA image determining process, for example.

Figure 9:
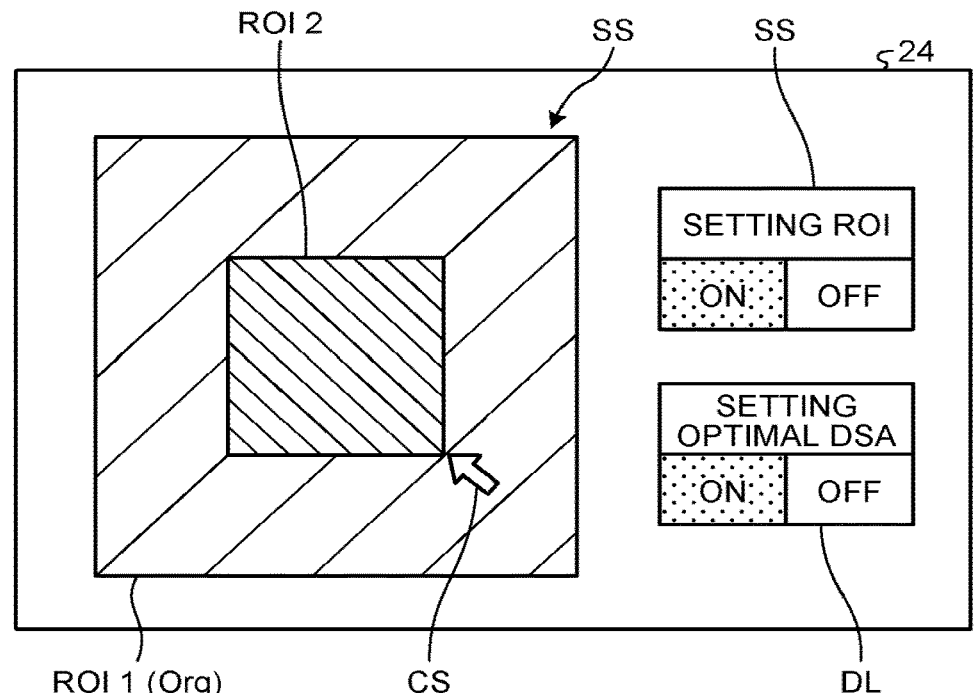
FIG. 9 is a drawing according to a fifth modification example of the embodiment illustrating an example of a user interface related to a setting for a region of interest and a setting for a DSA image determining process.

FIG. 9 is a drawing illustrating an example of a user interface related to a setting for the region of interest and a setting for the DSA image determining process. As illustrated in FIG. 9, the display 24 is configured to display a dialog DL related to selecting whether or not performing registration is required, together with a setting screen SS for a region of interest in the one contrast image. When the option "SETTING ROI" is turned on, as illustrated in FIG. 9, it is possible to set a ROI by operating a cursor CS. Further, when the option to set a region of interest is selected, the display 24 is configured to display the one subtraction image together with ROI1(Org), as illustrated in FIG. 9.

On the display screen illustrated in FIG. 9, the user inputs, through the input interface 23, the ON/OFF setting for the region of interest and the ON/OFF setting for the DSA image determining process. In FIG. 9, the option to set a region of interest (ROI) is turned on, so that a second region of interest ROI2 is set with respect to a normal region of interest ROI1(Org) set as a default. Further, as illustrated in FIG. 9, the option to display an optimal DSA indicating a setting for the DSA image determining process is turned on.

By employing the registration function 26d, the processing circuitry 26 is configured to perform registration between the plurality of regions of interest set in the one contrast image selected by the user and each of the plurality of mask images. In other words, the registration function 26d is configured to perform the registration by using the regions of interest as regions subject to the registration. The process performed by the registration function 26d is carried out at step S304 in FIG. 3 included in the DSA image determining process, for example.

By employing the matching degree calculating function 26e, on the basis of the plurality of mask images and a plurality of region-of-interest images corresponding to the plurality of regions of interest registered with each other, the processing circuitry 26 is configured to calculate a plurality of matching degrees between the plurality of mask images and the plurality of region-of-interest images registered with each other. More specifically, the matching degree calculating function 26e is configured to calculate a plurality of difference images between the region-of-interest images and the plurality of mask images, in accordance with the set regions of interest. Subsequently, the matching degree calculating function 26e is configured to calculate a plurality of matching degrees with respect to each of the regions of interest, while using the regions of interest in the plurality of difference images as targets of the calculation.

That is to say, the matching degree calculating function 26e is configured to calculate the plurality of matching degrees, by using each region of interest as a matching degree calculation area, within the plurality of difference images indicating the differences between the plurality of mask images and the one contrast image registered in accordance with the regions of interest. In other words, with respect to each of the plurality of regions of interest, the matching degree calculating function 26e is configured to calculate the plurality of matching degrees on the basis of the plurality of difference images. The process performed by the matching degree calculating function 26e is carried out at step S305 in FIG. 3 included in the DSA image determining process, for example.

By employing the determining function 26f, the processing circuitry 26 is configured to determine the differences between the plurality of mask images corresponding to the maximum matching degrees respectively related to the plurality of regions of interest and the plurality of region-ofinterest images, as a plurality of subtraction images of interest corresponding to the plurality of regions of interest. In other words, with respect to each of the plurality of regions of interest, the determining function 26*f* is configured to determine the difference image between the mask image related to the maximum matching degree and the one contrast image, as a subtraction image of interest. The process performed by the determining function 26*f* is carried out at step S306 in FIG. 3 included in the DSA image determining process, for example.

The display 24 is configured to display the one subtraction image determined in the embodiment and the plurality of subtraction images of interest. The process performed by the display 24 is carried out at step S307 in FIG. 3 included in the DSA image determining process, for example.

Figure 10:
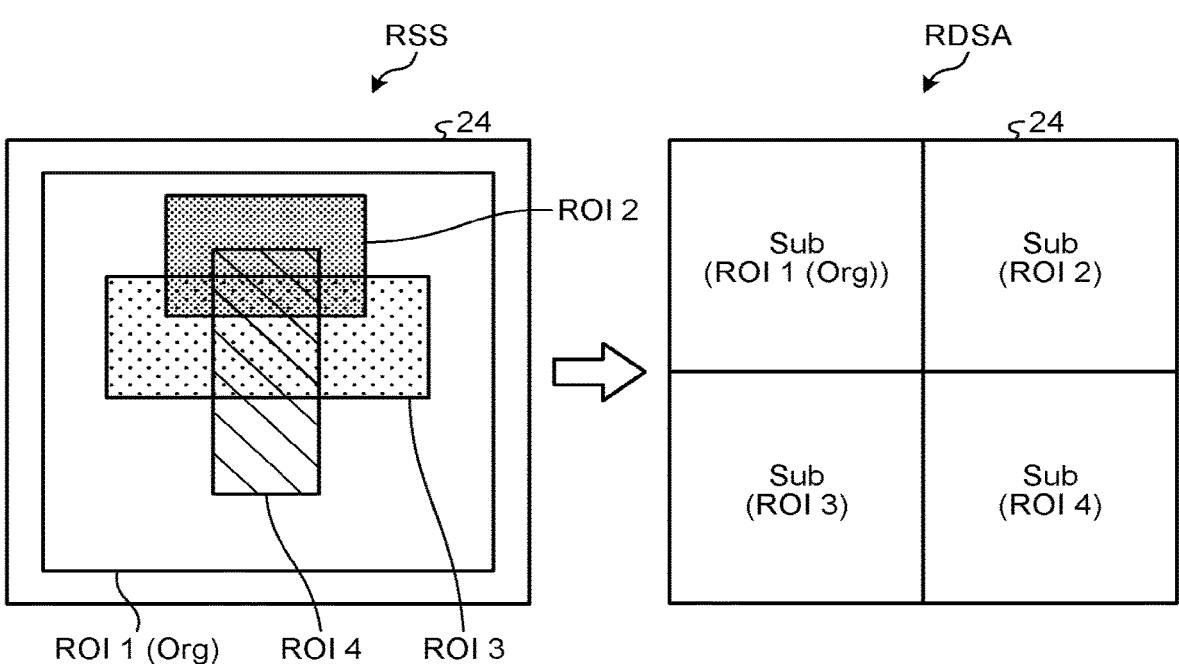
FIG. 10 is a drawing according to the fifth modification example of the embodiment illustrating an example indicating a plurality of Regions Of Interest (ROIs) that are set and a plurality of subtraction images displayed on the display in accordance with the plurality of ROIs.

FIG. 10 is a drawing illustrating an example RDSA indicating a plurality of ROIs (the ROI1(Org), ROI2, ROI3, and ROI4) that are set and a plurality of subtraction images displayed on the display 24 in accordance with the plurality of ROIs. The subtraction image Sub(ROI1(Org)) illustrated in FIG. 10 is a subtraction image between the mask image corresponding to the maximum matching degree and having been registered and the one contrast image, with respect to the region of interest ROI1(Org). The subtraction image Sub(ROI2) illustrated in FIG. 10 is a subtraction image between the mask image corresponding to the maximum matching degree and having been registered and the one contrast image, with respect to the region of interest ROI2.

The subtraction image Sub(ROI3) illustrated in FIG. 10 is a subtraction image between the mask image corresponding to the maximum matching degree and having been registered and the one contrast image, with respect to the region of interest ROI3. The subtraction image Sub(ROI4) illustrated in FIG. 10 is a subtraction image between the mask image corresponding to the maximum matching degree and having been registered and the one contrast image, with respect to the region of interest ROI4. As illustrated in FIG. 10, the user will select a DSA image from among the plurality of subtraction images displayed in the RDSA, via the input interface 23.

The X-ray diagnosis apparatus 1 according to the present modification example is configured to perform the registration between the plurality of regions of interest set in the one contrast image and each of the plurality of mask images; to calculate the plurality of matching degrees between the plurality of mask images and the plurality of region-of-interest images registered with each other, on the basis of the plurality of mask images and the plurality of region-of-interest images corresponding to the plurality of regions of interest registered with each other; to determine the differences between the plurality of mask images corresponding to the maximum matching degree with respect to each of the plurality of regions of interest and the one contrast image, as the plurality of subtraction images of interest corresponding to the plurality of regions of interest; and to display the one subtraction image and the plurality of subtraction images of interest.

With this arrangement, the X-ray diagnosis apparatus 1 in the present example is capable of causing the display 24 to display the subtraction images using the mask image corresponding to the maximum matching degree with respect to each of the plurality of regions of interest set in the one contrast image. Consequently, the X-ray diagnosis apparatus 1 is able to present the user with the candidates for the subtraction image having little misregistration in accordance with the regions of interest. Because the other advantageous effects are the same as those of the embodiment, explanations thereof will be omitted.

Sixth Modification Example

The present modification example is obtained by configuring the embodiment so that a contrast region related to the contrast agent is extracted on the basis of the subtraction image related to the maximum matching degree, so as to apply the DSA image determining process to the extracted contrast region. In other words, in the present modification example, registration is performed between a contrast partial image using the extracted contrast region as a region of interest and the plurality of mask images, so as to re-calculate matching degrees between the plurality of mask images and the contrast partial image.

Subsequently, in the present modification example, the DSA image determining process is performed in the same manner as in the embodiment and the first to the fifth modification examples, by using the re-calculated matching degrees. In other words, in the present modification example, the plurality of matching degrees are re-calculated, on the basis of the contrast partial image corresponding to the contrast region extracted from the subtraction image related to the maximum matching degree among the plurality of matching degrees and the plurality of mask images.

By employing the registration function 26*d*, on the basis of the subtraction image calculated from the mask image having the maximum matching degree and the one contrast image selected by the user and the one contrast image, the processing circuitry 26 is configured to extract the contrast region related to the contrast agent from the subtraction image. The registration function 26*d* is configured to perform the registration between the contrast partial image corresponding to the contrast region and the plurality of mask images. For example, the registration function 26*d* is configured to perform the registration by applying at least one transformation selected from between translation and rotation to the plurality of mask images, on the basis of the contrast partial image and each of the plurality of mask images, for example. The process performed by the registration function 26*d* is carried out after step S306 in FIG. 3 included in the DSA image determining process, for example.

By employing the matching degree calculating function 26*e*, the processing circuitry 26 is configured to calculate the plurality of matching degrees between the contrast partial image and the plurality of mask images, by using the plurality of mask images used for the registration with the contrast partial image and the contrast partial image. In other words, with respect to the extracted contrast region, the matching degree calculating function 26*e* is configured to re-calculate the plurality of matching degrees respectively corresponding to the plurality of mask images, on the basis of a plurality of difference images between the plurality of mask images and the contrast partial image registered with each other. The process performed by the matching degree calculating function 26*e* is carried out after the abovementioned process performed by the registration function 26*d* in the present modification example, during the DSA image determining process, for example.

By employing the determining function 26*f*, the processing circuitry 26 is configured to determine the difference between one of the mask images corresponding to the maximum matching degree among the re-calculated plurality of matching degrees and the one contrast image, as one subtraction image corresponding to the one contrast image. In other words, the determining function 26*f* is configured to determine a difference image related to the maximum matching degree among the plurality of difference images, as the subtraction image. The process performed by the determining function 26*f* is carried out after the abovementioned process performed by the matching degree calculating function 26*e* in the present modification example, during the DSA image determining process, for example. After the process performed by the determining function 26*f*, the process at step S307 in FIG. 3 is performed.

The X-ray diagnosis apparatus 1 according to the present modification example is configured: to extract the contrast region related to the contrast agent from the subtraction image on the basis of the subtraction image and the one contrast image; to perform the registration between the contrast partial image corresponding to the contrast region and the plurality of mask images; to re-calculate the plurality of matching degrees between the contrast partial image and the plurality of mask images, by using the plurality of mask images used for the registration with the contrast partial image and the contrast partial image; and to determine the difference between the one of the mask images corresponding to the maximum matching degree among the re-calculated plurality of matching degrees and the one contrast image, as the one subtraction image corresponding to the one contrast image.

The X-ray diagnosis apparatus 1 according to the present modification example is configured: to extract the contrast region related to the contrast agent from the subtraction image, on the basis of the subtraction image related to the maximum matching degree determined in the embodiment and the one contrast image; to perform the registration between the contrast partial image corresponding to the contrast region and the plurality of mask images; to re-calculate the plurality of matching degrees between the contrast partial image and the plurality of mask images, by using the plurality of mask images used for the registration with the contrast partial image and the contrast partial image; and to determine the difference (the difference image) between the mask image corresponding to the maximum matching degree among the re-calculated plurality of matching degrees and having been registered and the one contrast image, as the one subtraction image corresponding to the one contrast image.

With this arrangement, because the extracted contrast region is used as the region of interest, the X-ray diagnosis apparatus 1 according to the present modification example is able to present the user with the candidates for the subtraction image having little misregistration in accordance with the contrast region. Because the other advantageous effects are the same as those of the embodiment, explanations thereof will be omitted.

Seventh Modification Example

In the present modification example, the one contrast image selected by the user is divided into a plurality of regions, so that the DSA image determining process is applied to each of a plurality of contrast sectional images corresponding to the plurality of regions resulting from the division. The quantity of the plurality of regions and the dividing method are set in advance. In the following sections, to explain a specific example, the plurality of regions are assumed to be three regions, whereas the dividing method is to divide the one contrast image into three slices from the bottom toward the top thereof. Further, the plurality of regions may be changed as appropriate, according to a user instruction received via the input interface 23.

By employing the registration function 26*d*, the processing circuitry 26 is configured to divide the one contrast image into the plurality of regions. The registration function 26*d* is configured to perform registration between the plurality of contrast sectional images corresponding to the plurality of regions and each of the plurality of mask images. More specifically, the registration function 26*d* is configured to perform the registration between a ROI set in each of the plurality of contrast sectional images and the plurality of mask images. The process performed by the registration function 26*d* is carried out at step S304 in FIG. 3 included in the DSA image determining process, for example.

By employing the matching degree calculating function 26*e*, the processing circuitry 26 is configured to calculate a plurality of matching degrees between the plurality of mask images and the plurality of contrast sectional images registered with each other, on the basis of the plurality of mask images and the plurality of contrast sectional images registered with each other. More specifically, the matching degree calculating function 26*e* is configured to generate a plurality of difference images indicating differences between the plurality of mask images and the plurality of contrast sectional images registered with each other. With respect to each of the plurality of regions, the matching degree calculating function 26*e* is configured to calculate a plurality of matching degrees respectively corresponding to the plurality of difference images, on the basis of the plurality of difference images. In other words, with respect to each of the plurality of regions, the matching degree calculating function 26*e* is configured to calculate the plurality of matching degrees. The process performed by the matching degree calculating function 26*e* is carried out at step S305 in FIG. 3 included in the DSA image determining process, for example.

By employing the determining function 26*f*, the processing circuitry 26 is configured, in accordance with the plurality of regions, to determine the differences between the mask image corresponding to the maximum matching degree and the plurality of contrast sectional images, as a plurality of sectional subtraction images. In other words, with respect to each of the plurality of regions, the determining function 26*f* is configured to determine a difference image related to the maximum matching degree among the plurality of matching degrees, as the sectional subtraction image. That is to say, the determining function 26*f* is configured to determine the plurality of sectional subtraction images corresponding to the plurality of regions, by using the maximum matching degree corresponding to each of the plurality of regions among the plurality of matching degrees. The determining function 26*f* is configured to generate one subtraction image corresponding to the one contrast image, by joining together the plurality of sectional subtraction images. The process performed by the determining function 26*f* is carried out at step S306 in FIG. 3 included in the DSA image determining process, for example.

Figure 11:
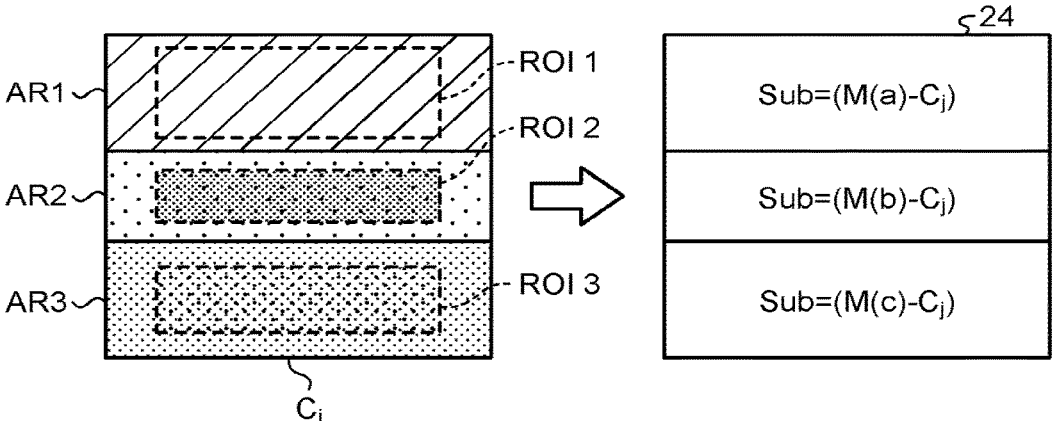
FIG. 11 is a drawing according to a seventh modification example of the embodiment illustrating an example indicating a plurality of regions obtained by dividing one contrast image and one subtraction image displayed on the display.

The display 24 is configured to display the one subtraction image. FIG. 11 is a drawing illustrating an example indicating a plurality of regions (AR1, AR2, and AR3) obtained by dividing the one contrast image C*j* and the one subtraction image displayed on the display 24. In FIG. 11, the first region AR1 is set with a first region of interest ROI1; the second region AR2 is set with a second region of interest ROI2; and the third region AR3 is set with a third region of interest ROI3. Each of the regions of interest is used for the registration with the plurality of mask images.

In FIG. 11, M(a) represents a region corresponding to the first region AR1 and denotes a mask image related to the maximum matching degree with respect to the first region of interest ROI1. In FIG. 11, M(b) represents a region corresponding to the second region AR2 and denotes a mask image related to the maximum matching degree with respect to the second region of interest ROI2. In FIG. 11, M(c) represents a region corresponding to the third region AR3 and denotes a mask image related to the maximum matching degree with respect to the third region of interest ROI3. As illustrated in FIG. 11, the one subtraction image corresponding to the one contrast image is obtained by joining (combining) together the three subtraction images Sub and is displayed on the display 24.

The X-ray diagnosis apparatus 1 according to the present modification example is configured: to divide the one contrast image selected by the user into the plurality of regions; to perform the registration between the plurality of contrast sectional images corresponding to the plurality of regions and each of the plurality of mask images; to calculate the plurality of matching degrees between the plurality of mask images and the plurality of contrast sectional images registered with each other, on the basis of the plurality of mask images and the plurality of contrast sectional images registered with each other; to determine, with respect to each of the plurality of regions, the differences (the difference images) between the mask image corresponding to the maximum matching degree and the plurality of contrast sectional images, as the plurality of sectional subtraction images; and to generate the one subtraction image by joining together the plurality of sectional subtraction images.

With this arrangement, the X-ray diagnosis apparatus 1 according to the present example is capable of causing the display 24 to display the one subtraction image, by joining together the sectional subtraction images obtained by using the mask image corresponding to the maximum matching degree with respect to each of the plurality of regions of interest into which the one contrast image was divided. Consequently, the X-ray diagnosis apparatus 1 is able to present the user with the candidates for the subtraction image having little misregistration in accordance with the plurality of regions resulting from the division. Because the other advantageous effects are the same as those of the embodiment, explanations thereof will be omitted.

Eighth Modification Example

The present modification example is related to an application to DSA (hereinafter "bolus DSA") related to bolus administration (or a bolus injection). In other words, the present modification example corresponds to an application of the first modification example to the bolus DSA. For example, the bolus DSA may be used in an X-ray imaging process for contrast-enhanced imaging of blood vessels in a leg of the patient P, for example.

Figure 12:
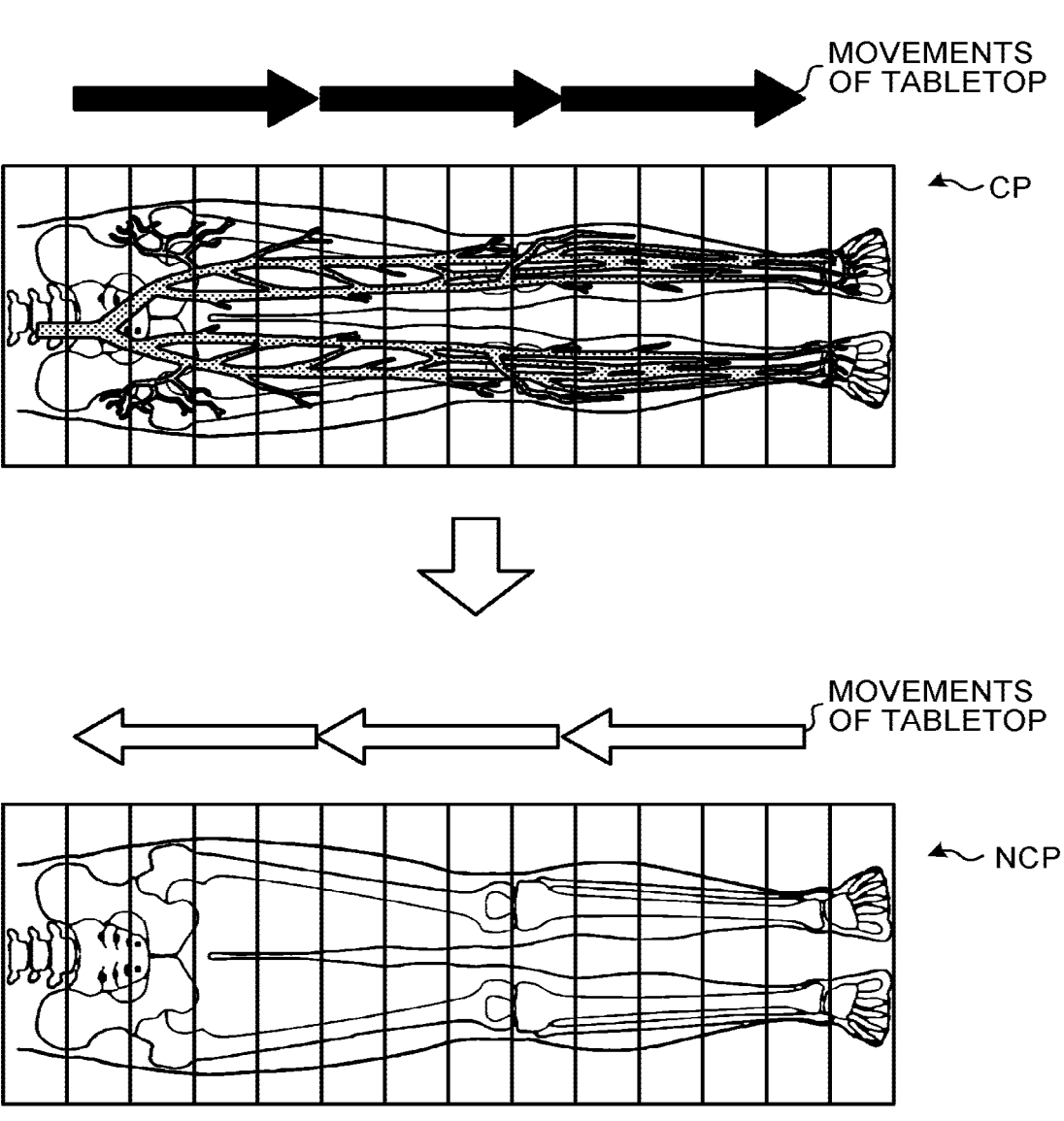
FIG. 12 is a drawing according to an eighth modification example of the embodiment illustrating an example of an outline of an imaging process related to bolus DSA.

FIG. 12 is a drawing illustrating an example of an outline of an imaging process related to the bolus DSA. As indicated as CP in FIG. 12, the system controlling unit 22 is configured to pan on the subject P following the contrast agent along the flow of the contrast agent. In this situation, the position data memory 21 is configured to store therein movements of the table 7 made while the contrast agent is being imaged. Further, by employing the image computing function 26a, the processing circuitry 26 is configured to generate a series of contrast images along the flow of the contrast agent. In other words, the plurality of contrast images serving as the series of contrast images are generated at a predetermined frame rate along the longitudinal direction of the patient P with bolus administration of the contrast agent for the patient P and include the one contrast image according to the embodiment.

Subsequently, as indicated as NCP in FIG. 12, the system controlling unit 22 is configured to pan on the patient P without using any contrast agent, by using the movements of the table 7 stored in the position data memory 21. In this situation, by employing the image computing function 26a, the processing circuitry 26 is configured to generate a series of mask images along the flow of the contrast agent. In other words, the plurality of mask images serving as the series of mask images are generated at substantially the same frame rate as that of the series of contrast images, in correspondence with the movements of the tabletop made at the time of acquiring the plurality of contrast images. Because it is possible to apply any of known techniques to the imaging procedure related to the bolus DSA, explanations thereof will be omitted.

By employing the registration function 26d, the processing circuitry 26 is configured to perform registration between each of the plurality of contrast images and one mask image (hereinafter "position correspondence mask image") among the plurality of mask images corresponding to the position of the tabletop related to a corresponding one of the plurality of contrast images and a plurality of mask images (hereinafter, "predetermined frame mask images") related to a predetermined number of frames (hereinafter, "predetermined frames") preceding and following the frame of the position correspondence mask image. The quantity of the predetermined number of frames in the present modification example is a value indicating the number of frames set in advance before the bolus DSA is carried out and may be set and changed as appropriate via the input interface 23.

More specifically, the registration function 26d is configured to perform the registration between the position correspondence mask image, the predetermined frame mask image, and each of the plurality of contrast images, with respect to the series of contrast images. The process performed by the registration function 26d is carried out at step S304 in FIG. 3 included in the DSA image determining process. Further, in an application example of the present modification example, the registration function 26d may be configured to perform registration with respect to a region of interest corresponding to a central part of each of the plurality of contrast images.

By employing the matching degree calculating function 26e, the processing circuitry 26 is configured, with respect to the plurality of contrast images, to calculate a plurality of matching degrees between each of the plurality of contrast images and the position correspondence mask image, the predetermined frame mask image, and the predetermined number of mask images. More specifically, the matching degree calculating function 26e is configured to generate a plurality of difference images indicating the differences between each of the plurality of contrast images, the position correspondence mask image, and the predetermined frame mask image. On the basis of the plurality of difference images, the matching degree calculating function 26e is configured to calculate the plurality of matching degrees respectively corresponding to the plurality of difference images, with respect to each of the plurality of contrast images.

The process performed by the matching degree calculating function 26e is carried out at step S305 in FIG. 3 included in the DSA image determining process. In this situation, when the registration was performed with respect to the region of interest corresponding to the central part of each of the plurality of contrast images, the matching degree calculating function 26e may calculate the matching degrees with respect to the regions of interest.

By employing the determining function 26f, the processing circuitry 26 is configured to determine the plurality of differences that are calculated with respect to the plurality of contrast images and that have the differences between the mask image corresponding to the maximum matching degree among the plurality of matching degrees and each of the plurality of contrast images, as a plurality of subtraction images corresponding to the plurality of contrast images. More specifically, with respect to each of the plurality of contrast images, the determining function 26f is configured to determine the difference image related to the maximum matching degree as a subtraction image. The determining function 26f is configured to determine the plurality of subtraction images corresponding to the plurality of contrast images, by performing the subtraction image determining process with respect to the plurality of contrast images.

By employing the determining function 26f, the processing circuitry 26 is configured to generate a long image by pasting together, along the longitudinal direction, the regions of interest in the plurality of subtraction images, on the basis of the determined plurality of subtraction images. More specifically, the determining function 26f is configured to generate the long image, by pasting together the plurality of regions of interest corresponding to central parts of the plurality of subtraction images, according to positions of the tabletop of the table 7. Alternatively, the process of pasting together the plurality of subtraction images may be carried out by the image computing function 26a. The abovementioned process performed by the determining function 26f is carried out at step S306 in FIG. 3 included in the DSA image determining process.

Figure 13:
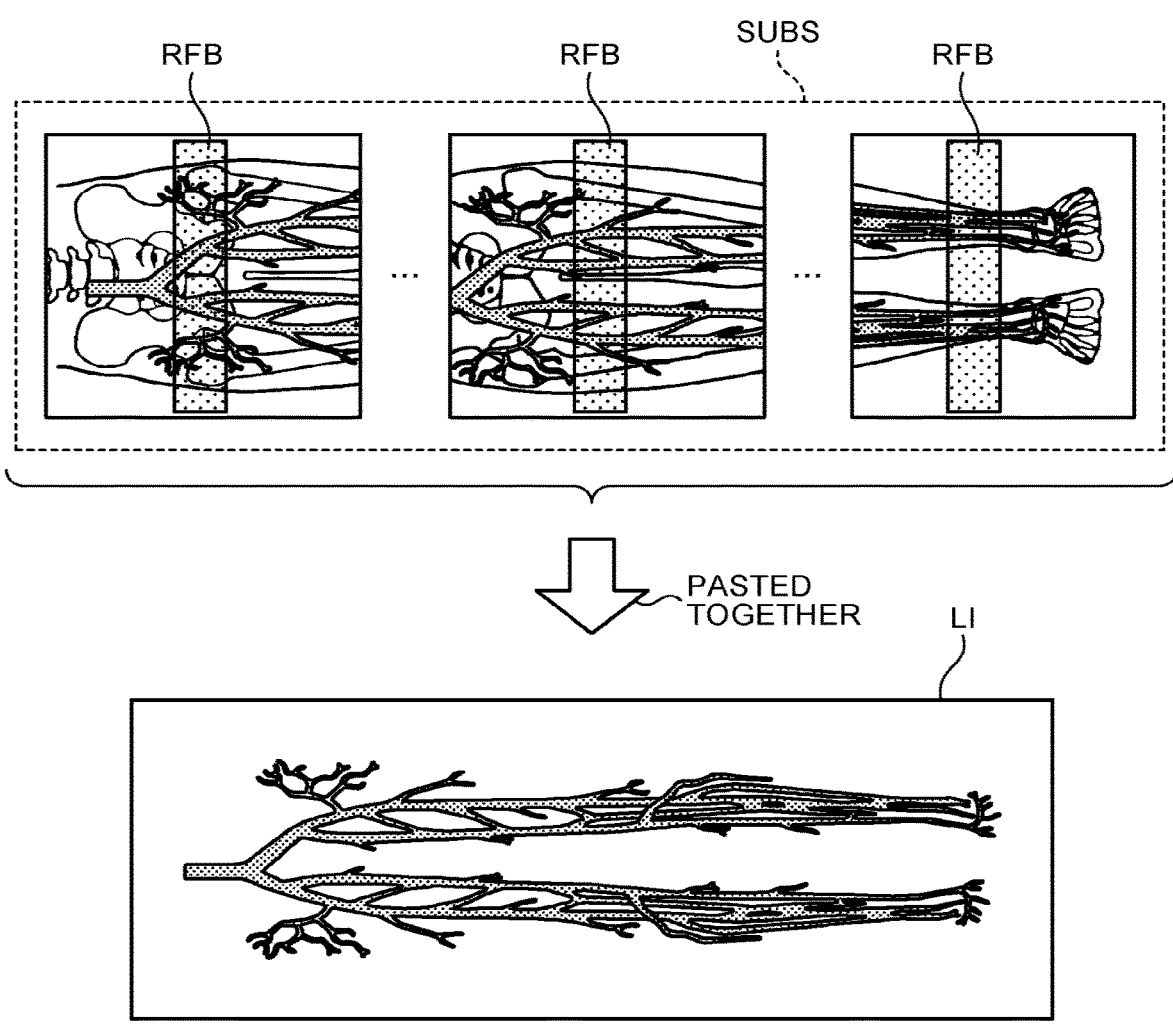
FIG. 13 is a drawing according to the eighth modification example of the embodiment illustrating an example of an outline of a long image generating process related to bolus DSA.

FIG. 13 is a drawing illustrating an example of an outline of the long image generating process related to the bolus DSA. As illustrated in FIG. 13, a long image LI related to the bolus DSA is generated by pasting together a plurality of regions of interest RFB related to the areas to be pasted together from the plurality of subtraction images SUBS. In an application example of the present modification example, two or more long images may be generated in descending order of the matching degrees. In that situation, the process performed by the determining function 26f is repeatedly performed, starting from the maximum matching degree until a predetermined matching degree is reached. In this situation, although the plurality of subtraction images SUBS in FIG. 13 render the bones in the background for the sake of convenience in the explanation, the bones in the background are either erased or attenuated in actuality by a subtraction process.

The display 24 is configured to display the generated long image LI. Alternatively, the display 24 may display two or more long images in descending order of the matching degrees. The abovementioned process performed by the display 24 is carried out at step S307 in FIG. 3 included in the DSA image determining process. When the two or more long images are displayed on the display 24, one of the long images selected by the user is stored, at step S307, into the memory 25 as an image related to the bolus DSA.

In the X-ray diagnosis apparatus 1 according to the present modification example, the one contrast image is included in the plurality of contrast images generated at the predetermined frame rate along the longitudinal direction of the patient P with the bolus administration of the contrast agent for the patient P, whereas the plurality of mask images are generated at the frame rate in correspondence with the movements of the table 7 at the time of acquiring the plurality of contrast images. In this situation, the X-ray diagnosis apparatus 1 according to the present modification example is configured to perform the registration between each of the plurality of contrast images and the one mask image among the plurality of mask images corresponding to the position of the tabletop related to a corresponding one of the plurality of contrast images and the predetermined number of mask images related to the predetermined number of frames preceding and following the frame related to the position of the tabletop.

Subsequently, the X-ray diagnosis apparatus 1 according to the present modification example is configured: to calculate, with respect to the plurality of contrast images, the plurality of matching degrees between each of the plurality of contrast images and the one mask image and the predetermined number of mask images; and to determine the plurality of differences that are calculated with respect to the plurality of contrast images and that have the differences between the mask image corresponding to the maximum matching degree among the plurality of matching degrees and each of the plurality of contrast images, as the plurality of subtraction images SUBS corresponding to the plurality of contrast images. Subsequently, the X-ray diagnosis apparatus 1 according to the present modification example is configured to generate the long image LI, by pasting together, along the longitudinal direction, the regions of interest in the plurality of subtraction images, on the basis of the plurality of subtraction images SUBS.

With these arrangements, even when misregistration may be caused by a state of the patient P and/or by a mechanical error such as the movements of the tabletop at the time of acquiring the series of contrast images and the series of mask images in the bolus DSA, the X-ray diagnosis apparatus 1 according to the present modification example is capable of generating an excellent DSA image. It is therefore possible to improve efficiency in diagnosing processes for the patient P and to improve a throughput of medical examinations. Because the other advantageous effects are the same as those of the embodiment, the first modification example, and the like, explanations thereof will be omitted.

Ninth Modification Example

In the present modification example, on the basis of two mask images that are temporally adjacent to each other among the plurality of mask images, a plurality of interpolation images included in the time width between the two mask images are generated, so as to perform the DSA image determining process by further using the generated interpolation images.

By employing the registration function 26d, the processing circuitry 26 is configured to generate the plurality of interpolation images included in the time width between the two mask images, on the basis of the two mask images that are temporally adjacent to each other. The plurality of interpolation images may be ten images, for example. The registration function 26d is configured to generate the plurality of interpolation images, by inputting the two mask images temporally adjacent to each other, to a trained model, for example. The plurality of interpolation images do not necessarily have to be generated by the trained model. For example, it is possible to use any of knowns technique such as a double speed frame interpolation, as appropriate. Accordingly, explanations about the process of generating the plurality of interpolation images will be omitted. The registration function 26d is configured to further perform registration between each of the plurality of interpolation images and the one contrast image. The process performed by the registration function 26d is carried out at step S304 in FIG. 3 included in the DSA image determining process, for example.

By employing the matching degree calculating function 26e, the processing circuitry 26 is configured to further calculate a plurality of matching degrees between the plurality of interpolation images and the one contrast image registered with each other, on the basis of the plurality of interpolation images and the one contrast image registered with each other. In other words, the matching degree calculating function 26e is configured to further generate a plurality of interpolation difference images, by calculating the differences between the plurality of interpolation images and the one contrast image registered with each other. Subsequently, the matching degree calculating function 26e is configured to calculate the plurality of matching degrees respectively corresponding to the plurality of interpolation difference images, by using a plurality of pixels in the plurality of interpolation difference images. The process performed by the matching degree calculating function 26e is carried out at step S305 in FIG. 3 included in the DSA image determining process, for example.

By employing the determining function 26f, the processing circuitry 26 is configured to determine the difference between either one of the mask images or one of the interpolation images corresponding to the maximum matching degree among the plurality of matching degrees and the one contrast image, as one subtraction image. The process performed by the determining function 26f is carried out at step S306 in FIG. 3 included in the DSA image determining process, for example.

The X-ray diagnosis apparatus 1 according to the present modification example is configured to generate the plurality of interpolation images included in the time width between the two mask images, on the basis of the two mask images that are temporally adjacent to each other among the plurality of mask images; to further perform the registration between each of the plurality of interpolation images and the one contrast image; to further calculate the plurality of matching degrees between the plurality of interpolation images and the one contrast image registered with each other, on the basis of the plurality of interpolation images and the one contrast image registered with each other; and to determine the difference (the difference image) between either the one of the mask images or the one of the interpolation images corresponding to the maximum matching degree among the plurality of matching degrees and the one contrast image, as the one subtraction image.

Alternatively, to generate the interpolation images, it is also acceptable to use three or more mask images. In that situation, it is possible to improve the level of precision of the interpolation process compared to the situation using two mask images.

With this arrangement, because there are a larger number of mask images for the plurality of matching degrees, the X-ray diagnosis apparatus 1 according to the present modification example is capable of determining an excellent DSA image having even less misregistration. Because the other advantageous effects are the same as those of the embodiment, explanations thereof will be omitted.

When technical concept of the embodiment is realized as a medical image processing apparatus, the medical image processing apparatus has the configuration illustrated inside the dotted-line box 110 in FIG. 1, for example. The medical image processing apparatus 110 is configured: to perform registration between one contrast image generated by performing an X-ray imaging process on the patient P and each of a plurality of mask images generated by performing an X-ray imaging process; to calculate a plurality of matching degrees between the plurality of mask images and the one contrast image registered with each other, on the basis of the plurality of mask images and the one contrast image registered with each other; and to determine the difference between the mask image corresponding to a maximum matching degree among the plurality of matching degrees and the one contrast image, as one subtraction image corresponding to the one contrast image. Because the processing procedure and advantageous effects of the DSA image determining process realized by the medical image processing apparatus 110 are the same as those of the embodiment and the like, explanations thereof will be omitted.

When technical concept of the embodiment is realized as a medical image processing program, the medical image processing program causes a computer to realize: performing registration between one contrast image and each of a plurality of mask images; calculating a plurality of matching degrees between the plurality of mask images and the one contrast image registered with each other, on the basis of the plurality of mask images and the one contrast image registered with each other; and determining the difference between the mask image corresponding to a maximum matching degree among the plurality of matching degrees and the one contrast image, as one subtraction image corresponding to the one contrast image.

For example, it is also possible to realize the DSA image determining process by installing the medical image processing program in a computer of the medical image processing apparatus, a server apparatus, or the like and loading the installed program into a memory. In that situation, the program capable of causing the computer to execute the DSA image determining process may be distributed as being stored in a storage medium such as a magnetic disk (e.g., a hard disk), an optical disk (e.g., a Compact Disk Read-Only Memory (CD-ROM), a Digital Versatile Disk (DVD), etc.), or a semiconductor memory. Because the processing procedure and advantageous effects of the DSA image determining process realized by the medical image processing program are the same as those of the embodiment, explanations thereof will be omitted.

According to at least one aspect of the embodiments and the like described above, it is possible to determine an excellent DSA image, while burdens imposed on the user operations are reduced.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus, comprising:
processing circuitry configured to
    perform registration between one contrast image and each of a plurality of mask images;
    calculate a plurality of matching degrees between the plurality of mask images and the one contrast image registered with each other, based on the plurality of mask images and the one contrast image registered with each other; and determine a difference between (1) one of the mask images corresponding to a maximum matching degree among the plurality of matching degrees, and (2) the one contrast image, to determine one subtraction image corresponding to the one contrast image, wherein the processing circuitry is further configured to determine differences between a predetermined number of the plurality of mask images having higher matching degrees, among the plurality of matching degrees, and the one contrast image, to determine a plurality of subtraction images including the one subtraction image, the medical image processing apparatus further comprises a display configured to display the determined plurality of subtraction images, and each of the plurality of displayed subtraction images is determined by the processing circuitry using a corresponding one of the predetermined number of the plurality of mask images.

2. The medical image processing apparatus according to claim 1, wherein the processing circuitry is further configured to perform the registration by applying at least one transformation selected from between translation and rotation to the plurality of mask images, based on the one contrast image and each of the plurality of mask images.

3. The medical image processing apparatus according to claim 1, wherein the plurality of mask images are a series of mask images generated at a predetermined frame rate, the processing circuitry is further configured to determine differences between two of the mask images corresponding to frames preceding and following the maximum matching degree and the one contrast image, to determine two subtraction images related to the two mask images, and the medical image processing apparatus further comprises the display, which is configured to display the one subtraction image and the two subtraction images.

4. The medical image processing apparatus according to claim 1, wherein the processing circuitry is further configured to perform registration between two contrast images corresponding to frames preceding and following the one contrast image and the plurality of mask images, the processing circuitry is further configured to calculate a plurality of matching degrees between the plurality of mask images and the two contrast images registered with each other, based on the plurality of mask images and the two contrast images registered with each other, the processing circuitry is further configured to determine differences between the two contrast images and two of the mask images respectively corresponding to maximum matching degrees related to the two contrast images, to determine two subtraction images related to the two contrast images in the preceding and following frames, and the medical image processing apparatus further comprises the display, which is configured to display the one subtraction image and the two subtraction images.

5. The medical image processing apparatus according to claim 4, wherein the processing circuitry is further configured to further determine differences between the predetermined number of the plurality of mask images having higher matching degrees among the plurality of matching degrees and the one contrast image and the two contrast images, to determine the plurality of subtraction images, and the display is configured to display the one subtraction image, the two subtraction images, and the plurality of subtraction images.

6. The medical image processing apparatus according to claim 4, wherein the plurality of mask images are a series of mask images generated at a predetermined frame rate, the processing circuitry is further configured to determine differences between a plurality of mask images corresponding to frames preceding and following the maximum matching degrees related to the two contrast images and the two contrast images, to determine a plurality of subtraction images related to the two mask images in the preceding and following frames, and the display is configured to display the one subtraction image, the two subtraction images, and the plurality of subtraction images.

7. The medical image processing apparatus according to claim 1, wherein the processing circuitry is further configured to perform registration between a plurality of regions of interest set in the one contrast image and each of the plurality of mask images, based on the registered plurality of mask images and a plurality of region-of-interest images corresponding to the plurality of regions of interest, the processing circuitry is further configured to calculate a plurality of matching degrees between the registered plurality of mask images and the plurality of region-of-interest images, the processing circuitry is further configured to determine differences between a plurality of mask images corresponding to maximum matching degrees respectively related to the plurality of regions of interest and the one contrast image, as a plurality of subtraction images of interest corresponding to the plurality of regions of interest, and the medical image processing apparatus further comprises the display, which is configured to display the one subtraction image and the plurality of subtraction images of interest.

8. The medical image processing apparatus according to claim 1, wherein the processing circuitry is further configured to:

extract a contrast region related to a contrast agent from the subtraction image, based on the subtraction image and the one contrast image;

perform registration between a contrast partial image corresponding to the contrast region and the plurality of mask images;

re-calculate a plurality of matching degrees between the contrast partial image and the plurality of mask images, by using the plurality of mask images used for the registration with the contrast partial image and the contrast partial image; and determine a difference between one of the mask images corresponding to a maximum matching degree among the re-calculated plurality of matching degrees and the one contrast image, to determine one subtraction image corresponding to the one contrast image.

9. The medical image processing apparatus according to claim 1, wherein the processing circuitry is further configured to:

divide the one contrast image into a plurality of regions;

perform registration between a plurality of contrast sectional images corresponding to the plurality of regions and each of the plurality of mask images;

calculate a plurality of matching degrees between the plurality of mask images and the plurality of contrast sectional images registered with each other, based on the plurality of mask images and the plurality of contrast sectional images registered with each other;

determine, with respect to each of the plurality of regions, a difference between one of the mask images corresponding to the maximum matching degree and the plurality of contrast sectional images, to determine a plurality of sectional subtraction images; and generate the one subtraction image by joining together the plurality of sectional subtraction images.

10. The medical image processing apparatus according to claim 1, wherein the one contrast image is included in a plurality of contrast images generated at a predetermined frame rate along a longitudinal direction of an examined subject with bolus administration of a contrast agent for the examined subject, the plurality of mask images are generated at the frame rate in correspondence with movements of a tabletop at the time of acquiring the plurality of contrast images, and the processing circuitry is configured to:

perform registration between each of the plurality of contrast images and one mask image among the plurality of mask images corresponding to a position of the tabletop related to a corresponding one of the plurality of contrast images and a predetermined number of mask images related to a predetermined number of frames preceding and following a frame related to the position of the tabletop;

calculate, with respect to the plurality of contrast images, a plurality of matching degrees between each of the plurality of contrast images and the one mask image and the predetermined number of mask images;

determine a plurality of differences that are calculated with respect to the plurality of contrast images and that have differences between the mask image corresponding to the maximum matching degree among the plurality of matching degrees and each of the plurality of contrast images, to determine a plurality of subtraction images corresponding to the plurality of contrast images; and generate a long image by pasting together, along the longitudinal direction, regions of interest in the plurality of subtraction images, based on the plurality of subtraction images.

11. The medical image processing apparatus according to claim 1, wherein the processing circuitry is further configured to:

generate, based on a basis of two mask images temporally adjacent to each other among the plurality of mask images, a plurality of interpolation images included in a time width between the two mask images;

perform registration between each of the plurality of interpolation images and the one contrast image;

calculate a plurality of matching degrees between the plurality of interpolation images and the one contrast image registered with each other, based on the plurality of interpolation images and the one contrast image registered with each other; and determine a difference between either one of the mask images or one of the interpolation images corresponding to a maximum matching degree among the plurality of matching degrees and the one contrast image, as the one subtraction image.

12. The medical image processing apparatus according to claim 1, wherein the display is configured to display a dialog related to selecting whether or not the registration is required, together with a screen for setting a region of interest in the one contrast image, and the display is configured to display the one subtraction image when setting the region of interest is selected.

13. An X-ray diagnosis apparatus, comprising:

processing circuitry configured to perform registration between one contrast image generated by performing an X-ray imaging process on an examined subject and each of a plurality of mask images generated by the X-ray imaging process;

calculate a plurality of matching degrees between the plurality of mask images and the one contrast image registered with each other, based on the plurality of mask images and the one contrast image registered with each other; and determine a difference between (1) one of the mask images corresponding to a maximum matching degree among the plurality of matching degrees, and (2) the one contrast image, to determine one subtraction image corresponding to the one contrast image, wherein the processing circuitry is further configured to determine differences between a predetermined number of the plurality of mask images having higher matching degrees, among the plurality of matching degrees, and the one contrast image, to determine a plurality of subtraction images including the one subtraction image, the X-ray diagnosis apparatus further comprises a display configured to display the determined plurality of subtraction images, and each of the plurality of displayed subtraction images is determined by the processing circuitry using a corresponding one of the predetermined number of the plurality of mask images.

14. A non-volatile computer-readable storage medium storing therein a medical image processing program that causes a computer to perform a method comprising:

performing registration between one contrast image and each of a plurality of mask images;

calculating a plurality of matching degrees between the plurality of mask images and the one contrast image registered with each other, based on the plurality of mask images and the one contrast image registered with each other; and determining a difference between (1) one of the mask images corresponding to a maximum matching degree among the plurality of matching degrees, and (2) the one contrast image, to determine one subtraction image corresponding to the one contrast image, wherein the method further comprises determining differences between a predetermined number of the plurality of mask images having higher matching degrees, among the plurality of matching degrees, and the one contrast image, to determine a plurality of subtraction images including the one subtraction image, displaying the determined plurality of subtraction images, wherein each of the plurality of displayed subtraction images is determined using a corresponding one of the predetermined number of the plurality of mask images.

* * * * *